United States Patent
Iijima et al.

(10) Patent No.: US 11,147,862 B2
(45) Date of Patent: Oct. 19, 2021

(54) CD4 T CELLS PROVIDE ANTIBODY ACCESS TO IMMUNOPRIVILEGED TISSUE

(71) Applicant: Yale University, New Haven, CT (US)

(72) Inventors: Norifumi Iijima, Osaka (JP); Akiko Iwasaki, New Haven, CT (US)

(73) Assignee: Yale University, New Haven, CT (US)

(*) Notice: Subject to any disclaimer, the term of this patent is extended or adjusted under 35 U.S.C. 154(b) by 164 days.

(21) Appl. No.: 15/596,048

(22) Filed: May 16, 2017

(65) Prior Publication Data

US 2017/0326214 A1 Nov. 16, 2017

Related U.S. Application Data

(60) Provisional application No. 62/337,000, filed on May 16, 2016.

(51) Int. Cl.
| | |
|---|---|
| *A61K 39/395* | (2006.01) |
| *A61K 39/00* | (2006.01) |
| *A61K 35/12* | (2015.01) |
| *A61K 39/02* | (2006.01) |

(52) U.S. Cl.
CPC .......... *A61K 39/0011* (2013.01); *A61K 35/12* (2013.01); *A61K 39/0002* (2013.01); *A61K 39/0005* (2013.01); *A61K 39/0007* (2013.01); *A61K 39/02* (2013.01); *A61K 39/395* (2013.01); *A61K 39/00* (2013.01); *A61K 2035/122* (2013.01); *A61K 2039/5152* (2013.01); *A61K 2039/5156* (2013.01)

(58) Field of Classification Search
CPC ............ A61K 39/0002; A61K 39/0005; A61K 39/0007; A61K 39/0011; A61K 39/02; A61K 39/12
See application file for complete search history.

(56) References Cited

PUBLICATIONS

Hawkins et al., 2005, "The blood-brain barrier/neurovascular unit in health and disease." Pharmacol. Rev. 57, 173-185.
Weerasuriya, A. et al., 2011, "The blood-nerve barrier: structure and functional significance." Methods Mol. Biol. 686, 149-173.
Milligan, G. N. et al., 1998, "T lymphocytes are required for protection of the vaginal mucosae and sensory ganglia of immune mice against reinfection with herpes simplex virus type 2." J. Immunol. 160, 6093-6100.
Iijima, N. et al., 2014, "T cell memory. A local macrophage chemokine network sustains protective tissue-resident memory CD4 T cells." Science 346, 93-98.
Laidlaw, B. J. et al., 2014, "CD4+ T cell help guides formation of CD103+ lung-resident memory CD8+ T cells during influenza viral infection." Immunity 41, 633-645.
Iijima, N. et al., 2011, "Recruited inflammatory monocytes stimulate antiviral Th1 immunity in infected tissue." Proc. Natl Acad. Sci. USA 108, 284-289.
Johnson, A. J. et al., 2008, "Effector CD4+ T-cell involvement in clearance of infectious herpes simplex virus type 1 from sensory ganglia and spinal cords." J. Virol. 82, 9678-9688.
Knowland, D. et al., 2014, "Stepwise recruitment of transcellular and paracellular pathways underlies blood-brain barrier breakdown in stroke." Neuron 82, 603-617.
Koelle, D. M. et al., 2008, "Herpes simplex: insights on pathogenesis and possible vaccines." Annu. Rev. Med. 59, 381-395.
Knipe, D. M. et al., 2008, "Chromatin control of herpes simplex virus lytic and latent infection." Nature Rev. Microbiol. 6, 211-221.
Parr, M. B. et al., 1994, "A mouse model for studies of mucosal immunity to vaginal infection by herpes simplex virus type 2." Lab. Invest. 70, 369-380. Abstract only.
Parr, M. B. et al., 2000, "Immunity to vaginal herpes simplex virus-2 infection in B-cell knockout mice." Immunology 101, 126-131.
Sato, A. et al., 2014, "Vaginal memory T cells induced by intranasal vaccination are critical for protective T cell recruitment and prevention of genital HSV-2 disease." J. Virol. 88, 13699-13708.
Jones, C. A. et al., 2000, "Biological properties of herpes simplex virus 2 replication-defective mutant strains in a murine nasal infection model." Virology 278, 137-150.
Roopenian, D. C. et al., 2007, "FcRn: the neonatal Fc receptor comes of age." Nature Rev. Immunol. 7, 715-725.
McDermott, M. R. et al., 1990, "Mucosal and systemic antiviral antibodies in mice inoculated intravaginally with herpes simplex virus type 2." J. Gen. Virol. 71, 1497-1504.
Morrison, L. A. et al., 2001 "Vaccine-induced serum immunoglobin contributes to protection from herpes simplex virus type 2 genital infection in the presence of immune T cells." J. Virol. 75, 1195-1204.
Ohashi, M. et al., 2011, "Spread of herpes simplex virus to the spinal cord is independent of spread to dorsal root ganglia." J. Virol. 85, 3030-3032.
Anderson, K. G. et al., 2014. "Intravascular staining for discrimination of vascular and tissue leukocytes." Nature Protocols 9, 209-222.
Capaldo, C. T. et al. 2014, "Proinflammatory cytokine-induced tight junction remodeling through dynamic self-assembly of claudins." Mol. Biol. Cell 25, 2710-2719.
Reiss, C. S. et al., 1998, "Viral replication in olfactory receptor neurons and entry into the olfactory bulb and brain." Ann. NY Acad. Sci. 855, 751-761.
Thomsen, A. R. et al., 1997, "Cooperation of B cells and T cells is required for survival of mice infected with vesicular stomatitis virus." Int. Immunol. 9, 1757-1766.
Iijima, N. et al., 2008, "Dendritic cells and B cells maximize mucosal Th1 memory response to herpes simplex virus." J. Exp. Med. 205, 3041-3052.
Nakanishi, Y. et al., 2009, "CD8(+) T lymphocyte mobilization to virus-infected tissue requires CD4(+) T-cell help." Nature, 462, 510-513.

(Continued)

Primary Examiner — Robert C Hayes
(74) *Attorney, Agent, or Firm* — Riverside Law LLP

(57) ABSTRACT

The present disclosure relates to compositions and methods for treating or preventing a disease or disorder of immunoprivileged tissue. It is described herein that an immunogenic composition which induces production of memory CD4 T cells allows for the access of a therapeutic antibody to the immunoprivileged tissue.

11 Claims, 31 Drawing Sheets
Specification includes a Sequence Listing.

(56) References Cited

PUBLICATIONS

Reboldi, A. et al., 2009, "C—C chemokine receptor 6-regulated entry of TH-17 cells into the CNS through the choroid plexus is required for the initiation of EAE." Nature Immunol. 10, 514-523.
Stock, A. et al., 2014, "Type I IFN suppresses Cxcr2 driven neutrophil recruitment into the sensory ganglia during viral infection." J. Exp. Med. 211, 751-759.
Iwasaki, 2017, "Immune Regulation of Antibody Access to Neuronal Tissues." Trends in Molecular Medicine, 23(3): 227-245.
Wolf et al., 2010, "Natalizumab treatment in a patient with chronic inflammatory demyelinating polyneuropathy." Arch Neurol. 67(7), 881-883.
Vallat et al., 2015, "Natalizumab as a Disease-Modifying Therapy in Chronic Inflammatory Demyelinating Polyneuropathy—A Report of Three Cases." Eur. Neurol. 73(5-6), 294-302.

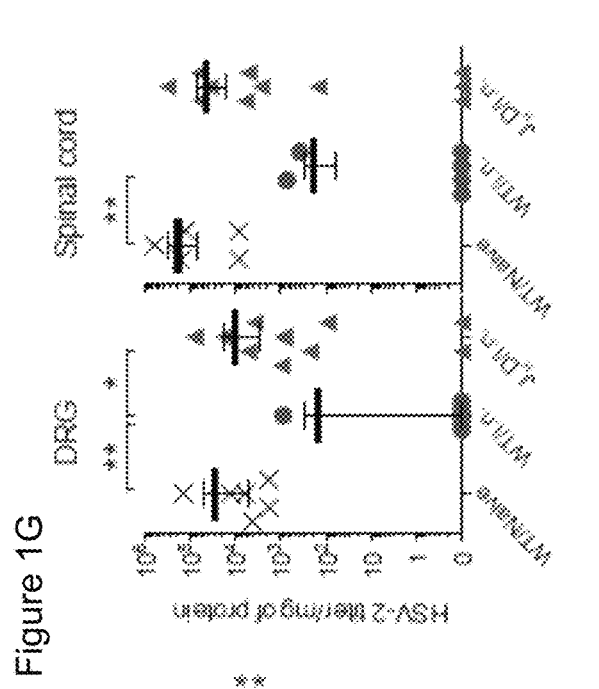
Figure 1G
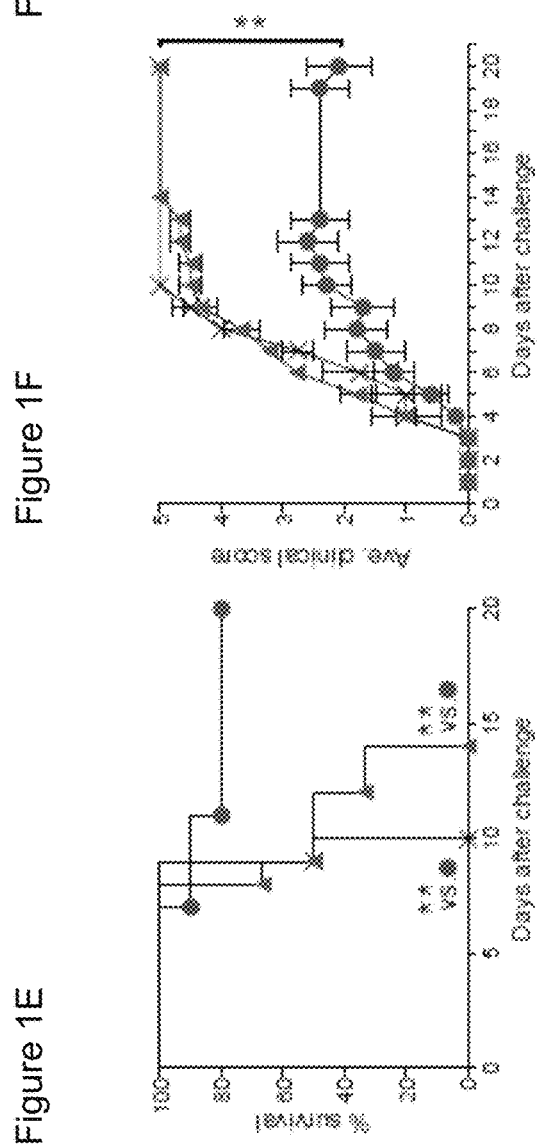
Figure 1F
Figure 1E

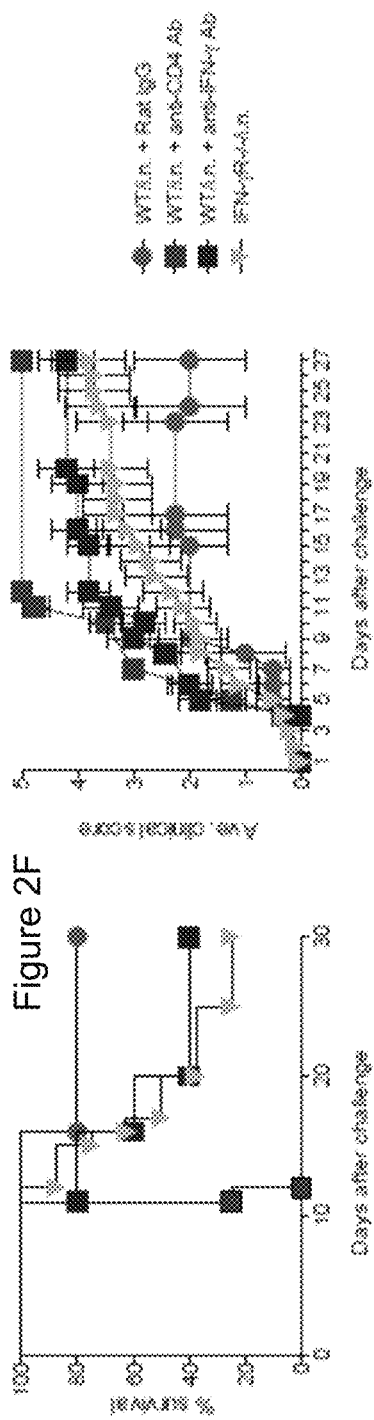
Figure 2E
Figure 2F
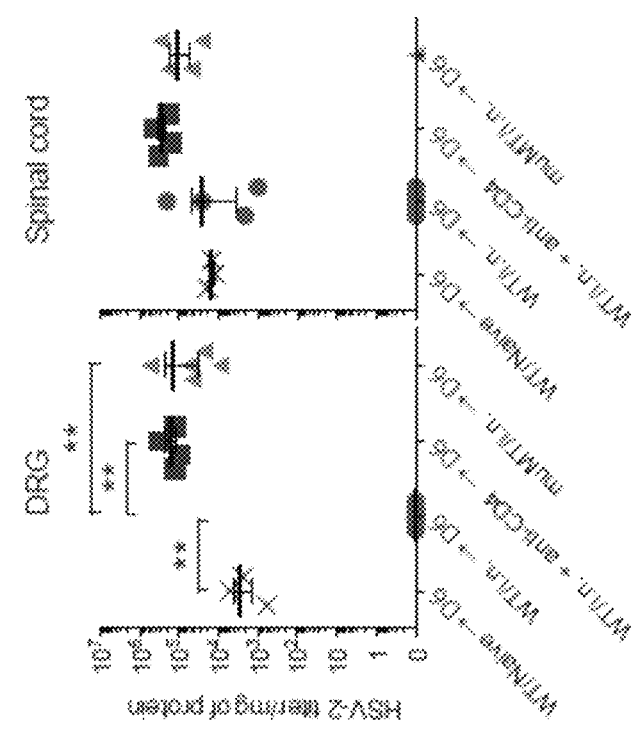
Figure 2G

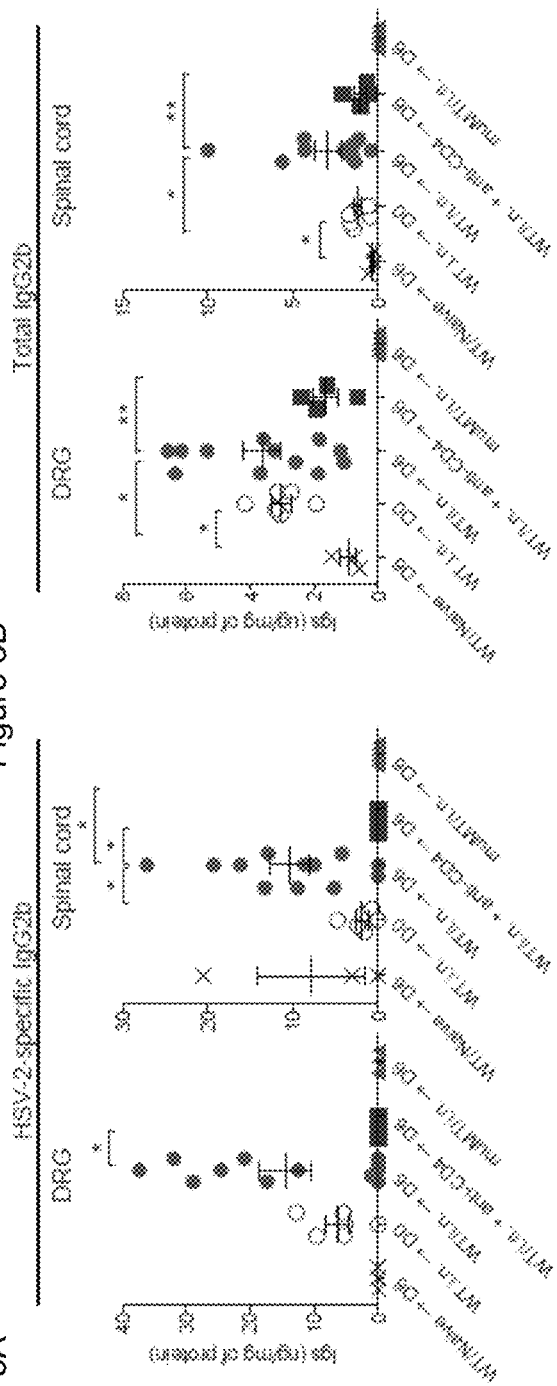
Figure 3A
Figure 3B
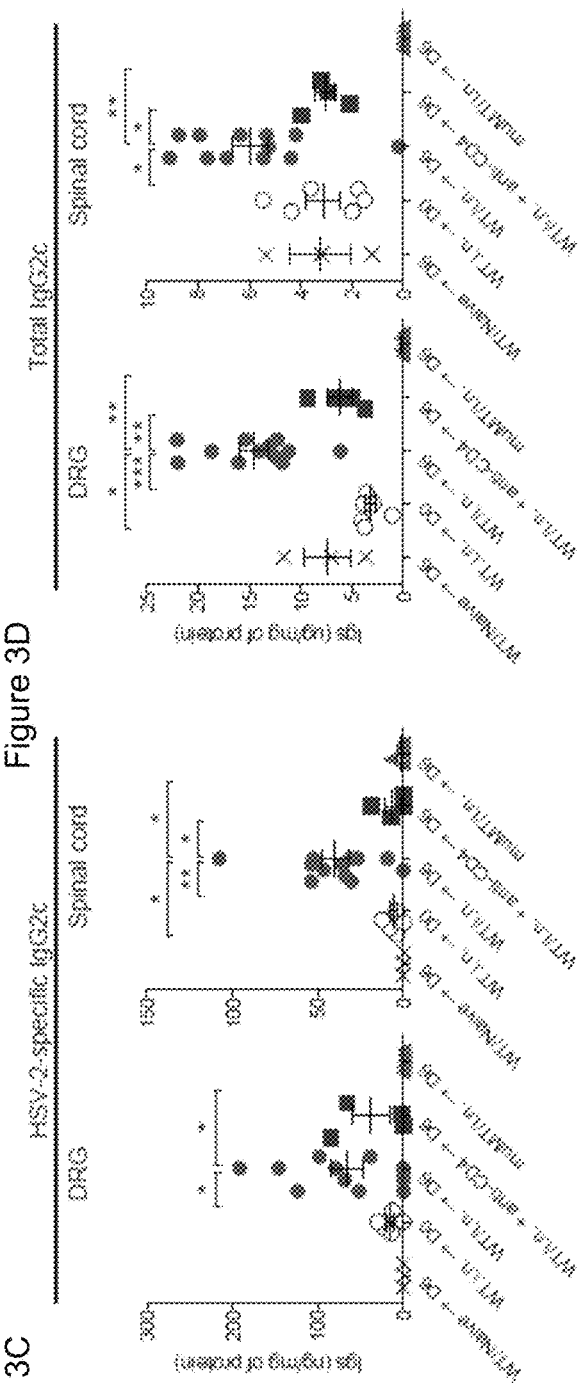
Figure 3C
Figure 3D

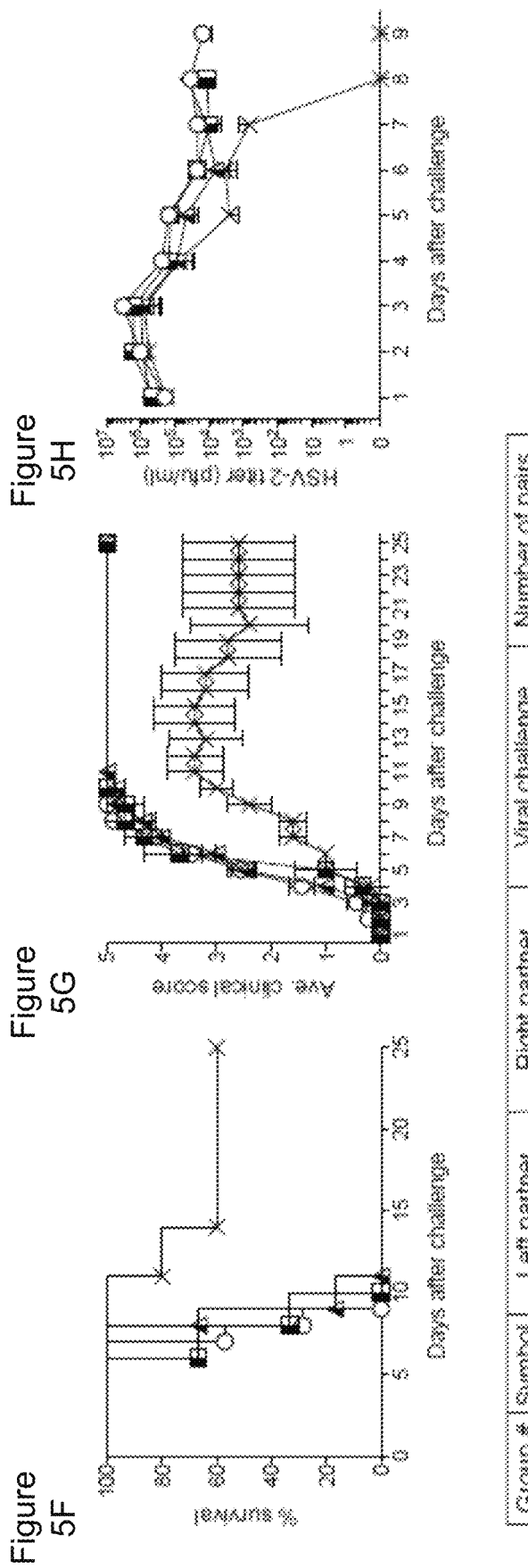

SEQUENCE LISTING

<160> NUMBER OF SEQ ID NOS: 2

<210> SEQ ID NO 1
<211> LENGTH: 20

-continued

```
<212> TYPE: DNA
<213> ORGANISM: Artificial Sequence
<220> FEATURE:
<223> OTHER INFORMATION: Chemically synthesized

<400> SEQUENCE: 1
agcgaggata acctgggatt                                                 20

<210> SEQ ID NO 2
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 2
gggataaagc ggggtaacat                                                 20
```

CD4 T CELLS PROVIDE ANTIBODY ACCESS TO IMMUNOPRIVILEGED TISSUE

CROSS-REFERENCE TO RELATED APPLICATIONS

The present application claims priority to U.S. Provisional Patent Application No. 62/337,000 filed May 16, 2016, which is hereby incorporated herein by reference in its entirety.

STATEMENT REGARDING FEDERALLY SPONSORED RESEARCH OR DEVELOPMENT

This invention was made with government support under AI064705, AI062428 and AI054359 awarded by National Institutes of Health. The government has certain rights in the invention.

BACKGROUND OF THE INVENTION

Circulating antibodies can access most tissues to mediate surveillance and elimination of invading pathogens. Immunoprivileged tissues such as the brain and the peripheral nervous system are shielded from plasma proteins by the blood-brain barrier (Hawkins et al., 2005, Pharmacol. Rev. 57, 173-185) and blood-nerve barrier (Weerasuriya, A. et al., 2011, Methods Mol. Biol. 686, 149-173), respectively. Yet, circulating antibodies must somehow gain access to these tissues to mediate their antimicrobial functions.

It is unclear how antibodies protect against pathogens that enter peripheral tissues devoid of constitutive antibody transport mechanisms. Blood brain barriers consisting of tight junction between capillary endothelial cells, thick basement membrane and astrocytes' foot processes effectively block the diffusion of antibodies to the brain (Weerasuriya, A. et al., 2011, Methods Mol. Biol. 686, 149-173), while blood nerve barriers consisting of endoneurial vascular endothelium and the perineurium block antibody access to the peripheral neurons 3. Such barriers are critical in preventing access by autoreactive antibodies (Milligan, G. N. et al., J. Immunol. 160, 6093-6100). At the same time, because certain pathogens target and replicate within immunoprivileged sites, a host mechanism to enable directed antibody delivery to these tissues must exist.

There is thus a need in the art for compositions and methods for treating and preventing infection of immunoprivileged sites. The present invention addresses this unmet need in the art.

SUMMARY OF THE INVENTION

In one aspect, the present invention provides a method for treating or preventing a disease or disorder of an immunoprivileged tissue in a subject in need thereof. In one embodiment, the method comprises administering an immunogenic agent to induce an immune response in the subject; and administering a therapeutic agent, whereby the immune response allows access of the therapeutic agent to the immunoprivileged tissue.

In one embodiment, the immunogenic agent is a vaccine. In one embodiment, the immunogenic agent comprises an antigen.

In one embodiment, the therapeutic agent is an antibody or antibody fragment that binds to an antigen associated with the disease or disorder. In one embodiment, the antigen associated with the disease or disorder is different from the antigen of the immunogenic agent. In one embodiment, the immune response comprises the activation or production of memory CD4 T cells.

In one embodiment, the disease or disorder comprises a pathogen-mediated infection selected from the group consisting of: a viral infection, a bacterial infection, a fungal infection, a protozoan infection, a prion infection, and a helminth infection. In one embodiment, the method treats or prevents infection-associated inflammation. In one embodiment, the method treats or prevents an infection-associated condition selected from the group consisting of: encephalitis, meningitis, meningoencephalitis, epidural abscess, subdural abscess, brain abscess, and progressive multifocal leukoencephalopathy (PML).

In one embodiment, the immunoprivileged tissue is selected from the group consisting of: brain, spinal cord, peripheral nervous system, testes, eye, placenta, and liver.

In one embodiment, the therapeutic agent comprises an antibody or antibody fragment that specifically binds a tumor-specific or tumor-associated antigen. In one embodiment, the method treats or prevents cancer.

In one embodiment, the therapeutic agent comprises an antibody or antibody fragment that specifically binds an antigen associated with a neurological disorder.

In one aspect, the present invention provides a composition for treating or preventing a disease or disorder of an immunoprivileged tissue in a subject in need thereof. In one embodiment, the composition comprises an immunogenic agent to induce an immune response in the subject; and a therapeutic agent.

In one embodiment, the immunogenic agent is a vaccine. In one embodiment, the immunogenic agent comprises an antigen.

In one embodiment, the therapeutic agent is an antibody or antibody fragment that binds to an antigen associated with the disease or disorder. In one embodiment, the antigen associated with the disease or disorder is different from the antigen of the immunogenic agent. In one embodiment, the immune response comprises the activation or production of memory CD4 T cells.

In one embodiment, the disease or disorder comprises a pathogen-mediated infection selected from the group consisting of: a viral infection, a bacterial infection, a fungal infection, a protozoan infection, a prion infection, and a helminth infection. In one embodiment, the immunoprivileged tissue is selected from the group consisting of: brain, spinal cord, peripheral nervous system, testes, eye, placenta, and liver.

In one embodiment, the therapeutic agent comprises an antibody or antibody fragment that specifically binds a tumor-specific or tumor-associated antigen. In one embodiment, the therapeutic agent comprises an antibody or antibody fragment that specifically binds an antigen associated with a neurological disorder.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1A through FIG. 1G are a set of images depicting the results of experiments demonstrating that intranasal immunization confers B-cell-dependent neuron protection following genital HSV-2 challenge. FIG. 1A through FIG. 1D:

C57/BL6 mice were immunized with TK− HSV-2 ($10^5$ plaque-forming units (p.f.u.)) via intranasal (i.n.; n=12), intraperitoneal (i.p.; n=5) or intravaginal (ivag.; n=11) routes. Five to 6 weeks later, these mice and naive mice (n=4) were challenged with a lethal dose of WT HSV-2 ($10^4$ p.f.u.). Mortality (FIG. 1A), clinical score (FIG. 1B) and virus titer in vaginal wash (FIG. 1C) were measured on indicated days after challenge. FIG. 1D: Six days after challenge, virus titer in tissue homogenates including DRG and spinal cord was measured. FIG. 1E through FIG. 1G: BALB/c mice (n=10) or B-cell-deficient JHD mice (n=6) were immunized intranasally with TK− HSV-2 ($5×10^4$ p.f.u.). Six weeks later, these mice and naive mice (n=4) were challenged with lethal WT HSV-2 ($10^5$ p.f.u.). Mortality (FIG. 1E) and clinical score (FIG. 1F) were measured. FIG. 1G: Six days after challenge, virus titer in tissue homogenates including DRG and spinal cord was measured by plaque assay. Data are means±s.e.m. *$P<0.05$; $P<0.01$; *$P<0.001$; ****$P<0.0001$ (two-tailed unpaired Student's t-test).

FIG. 2A through FIG. 2G are a set of images depicting the results of experiments demonstrating antibody-mediated neuroprotection on CD4 T cells but not on FcRn-mediated transport. FIG. 2A and FIG. 2B: C57/BL6 (WT) mice (n=4) and FcRn$^{-/-}$ (n=10) mice were immunized intranasally with TK− HSV-2 ($10^5$ p.f.u.), and 6 weeks later challenged with a lethal dose of WT HSV-2 ($10^4$ p.f.u.). Mortality (FIG. 2A) and clinical score (FIG. 2B) were measured. FIG. 2C and FIG. 2D: μMT mice were immunized with TK− HSV-2 ($10^5$ p.f.u.) intranasally. Five to 6 weeks later, naive mice (n=3), naive mice receiving immune serum intravenously (n=4), μMT mice (n=23) and μMT mice receiving immune serum intravenously (n=10) were challenged with a lethal dose of WT HSV-2, and mortality (FIG. 2C) and clinical score (FIG. 2D) were assessed. Immune serum prepared from mice immunized 4 weeks previously with TK− HSV-2 (200 μl per mouse) was injected 3 h before challenge, and 3 and 6 days after challenge. FIG. 2E & FIG. 2F, WT C57/BL6 mice (n=5) and IFN-γR$^{-/-}$ mice (n=8) immunized intranasally with TK− HSV-2 ($10^5$ p.f.u.) 6 weeks previously were challenged with a lethal dose of WT HSV-2, and mortality (FIG. 2E) and clinical score (FIG. 2F) were assessed. Depletion of CD4 T cells (n=4) or neutralization of IFN-γ (n=5) was performed on days −4, and −1, 2 and 4 days after challenge by intravenous injection of anti-CD4 (GK1.5) or anti-IFN-γ (XMG1.2), respectively. FIG. 2G: Six days after challenge, virus titer in tissue homogenates including DRG and spinal cord was measured by plaque assay (FIG. 2E). Data are means±s.e.m. *$P<0.05$; **$P<0.01$ (two-tailed unpaired Student's t-test).

FIG. 3A through FIG. 3D are a set of images depicting the results of experiments demonstrating that memory of CD4+ T cells are required for antibody access to neuronal tissues. Naive WT mice or WT and μMT mice intranasally immunized with TK− HSV-2 ($10^5$ p.f.u.) 6 weeks earlier were challenged with a lethal dose of WT HSV-2 intravaginally. Six days after the challenge, after extensive perfusion, HSV-2-specific (FIG. 3A, FIG. 3C) and total Ig (FIG. 3B, FIG. 3D) levels in tissue homogenates of DRG and spinal cord were analyzed by ELISA. To deplete CD4 T cells, CD4-specific antibody was injected on days −4, and −1, 2 and 4 days after challenge. Data are means±s.e.m. *$P<0.05$; $P<0.01$; *$P<0.001$ (two-tailed unpaired Student's t-test).

FIG. 4A: Six days after challenge, after extensive perfusion, HSV-2-specific IFN-γ$^+$ CD4$^+$ T cells in DRG and spinal cord were detected by flow cytometry. FIG. 4B: The number of IFN-γ-secreting CD4 T cells among 50,000 cells of CD45$^{hi}$ leukocytes in DRG and spinal cord is depicted. Data are means±s.e.m. *$P<0.05$; $P<0.01$; *$P<0.001$ (two-tailed unpaired Student's t-test). FIG. 4C: Frozen sections of DRG were stained with antibodies against CD4, VCAM-1 or CD31. Nuclei are depicted by 4', 6-diamidino-2-phenylindole (DAPI) stain (blue). Images were captured using a ×10 or ×40 objective lens. Scale bars, 100 μm. Arrowhead indicates VCAM-1$^-$ cells in parenchyma of DRG. Data are representative of at least three similar experiments. HSV-2-specific antibodies in the DRG (FIG. 4D) and spinal cord (FIG. 4E) were analyzed by ELISA. Data are means±s.e.m. *$P<0.05$ (two-tailed paired Student's t-test) Albumin level in tissue homogenates was analyzed by ELISA (FIG. 4F). Depletion of CD4 T cells or neutralization of IFN-γ was performed on days −4, and −1, 2 and 4 days after challenge by intravenous injection of anti-CD4 (GK1.5) or anti-IFN-γ (XMG1.2), respectively. Data are means±s.e.m. *$P<0.05$; $P<0.01$; *$P<0.001$ (two-tailed paired Student's t-test).

FIG. 5A through FIG. 5H are a set of images depicting the results of experiments demonstrating that in the absence of TRM, B cells are required for the protection of the host against genital HSV-2 challenge. FIG. 5A: C57BL/6 mice and μMT mice were immunized intravaginally or intranasally with TK− HSV-2. Five weeks later, vaginal tissue sections were stained for CD4$^+$ cells (red) and MHC class II$^+$ cells (green). Blue labelling depicts nuclear staining with DAPI (blue). Images were captured using a ×10 or ×40 objective lens. Scale bars, 100 μm. Data are representative of three similar experiments. FIG. 5B through FIG. D: BALB/c mice and JHD mice were immunized with TK− HSV-2 ($10^5$ p.f.u.) intranasally or intravaginally. Six weeks later, the number of total CD4+ T cells and HSV-2-specific IFN-γ$^+$ CD4$^+$ T cells in the vagina (FIG. 5B), spleen (FIG. 5C) and peripheral blood (FIG. 5D) were analyzed by flow cytometry. Percentages and total number of IFN-γ$^+$ cells among CD4$^+$CD90.2$^-$ cells are shown. Data are means±s.e.m. *$P<0.05$; $P<0.001$; *$P<0.001$ (two-tailed unpaired Student's t-test). FIG. 5E: C57/BL6 mice were immunized intravaginally (naive→D7) or intranasally (WT/i.n.→D0) with TK− HSV-2 virus. At the indicated time points (D7: 7 days after immunization; WT/i.n.→D0: 6 weeks after immunization), total viral genomic DNA in the vaginal tissues, DRG and spinal cord were measured by quantitative PCR. FIG. 5F-FIG. 5H: Intravaginally immunized C57BL/6 (WT), μMT and HEL-BCR Tg mice (left partner) were surgically joined with naive WT mice (right partner). Three weeks after parabiosis, the naive partner was challenged with a lethal dose of WT HSV-2 intravaginally. Mortality (FIG. 5E), clinical score (FIG. 5F) and virus titer in vaginal wash (FIG. 5G) following viral challenge are depicted.

FIG. 8A and FIG. 8B: WT mice immunized intranasally with TK– HSV-2 6-8 weeks earlier were challenged with a lethal dose of WT HSV-2. Depletion of CD4 T cells or neutralization of IFN-γ was performed on days –4, and –1, 2 and 4 days after challenge by intravenous injection of anti-CD4 (GK1.5) or anti-IFN-γ (XMG1.2), respectively. At time points indicated, HSV-2-specific Ig in the blood (n=4) (FIG. 8A) and total Ig in the blood (n=4) (FIG. 8B) were measured. FIG. 8C and FIG. 8D: WT mice immunized intranasally with TK– HSV-2 6 weeks earlier were challenged with a lethal dose of WT HSV-2. Neutralization of α4-integrin was performed on days 2 and 4 after challenge by intravenous injection of anti-α4-integrin/CD49b antibody. Six days later, HSV-2-specific antibody (FIG. 8C) and total antibody (FIG. 8D) in the blood were measured. Data are representative of three similar experiments.

FIG. 9A, C57BL/6 mice were immunized with a sublethal dose of influenza A/PR8 virus (10 p.f.u. per mouse) intranasally. Three weeks later, Flu-specific IFN-γ+ CD4+ T cells in spleen and neuronal tissues (DRG and spinal cord) (CD45.2+) following co-culture with HI-Flu/PR8 loaded splenocytes (CD45.1+) were analyzed by flow cytometry. As a control, lymphocytes isolated from spleen of TK– HSV-2 intranasally immunized mice 6 weeks after vaccination were used for co-culture. (***P<0.001; two-tailed unpaired Student's t-test). FIG. 9B through FIG. 9D: C57BL/6 mice were immunized with a sublethal dose of influenza A/PR8 virus (10 p.f.u. per mouse). Four weeks later, these mice were challenged with a lethal dose of WT HSV-2 ($10^4$ p.f.u. per mouse) intravaginally. Six days after challenge, total antibodies in lysate in DRG (FIG. 9B), spinal cord (FIG. 9C) and blood (FIG. 9D) were measured by ELISA.

FIG. 10A: C57BL/6 mice were immunized intranasally with TK– HSV-2. Six days after challenge of immunized mice 6 weeks prior, neuronal tissue sections (DRG and spinal cord) were stained for CD4+ cells and VCAM-1+ cells or CD31+ cells (red or green). Blue labelling depicts nuclear staining with DAPI (blue). Images were captured using a ×10 or ×40 objective lens. Scale bars, 100 μm. FIG. 10B: C57BL/6 mice were immunized intranasally with TK– HSV-2. Six weeks later, mice were challenged with WT HSV-2 intravaginal and neuronal tissues were collected 6 days later. DRG and spinal cord were stained for CD4+ cells (red) and MHC class II+ cells, CD11b+ cells or Ly6G+ cells (green). Blue labelling depicts nuclear staining with DAPI (blue). Images were captured using a ×10 or ×40 objective lens. Scale bars, 100 μm. Data are representative of at least three similar experiments.

FIG. 11A and FIG. 11B: C57BL/6 mice immunized intranasally with TK– HSV-2 6 weeks previously were challenged with lethal WT HSV-2. Six days after challenge, Alexa Fluor 700-conjugated anti-CD90.2 antibody (3 μg per mouse) was injected intravenously (tail vain) into immunized mice. Five minutes later, these mice were killed for fluorescence-activated cell sorting analysis of intravascular versus extravascular lymphocytes. Data are representative of at least two similar experiments.

FIG. 12A, WT mice immunized with TK– HSV-2 ($10^5$ p.f.u.) intranasally 6 weeks earlier were injected intravaginally with recombinant mouse IFN-γ (10 μg per mouse) (n=3) or PBS (n=3). At the indicated time points, HSV-2-specific Ig (FIG. 12A) and total Ig (FIG. 12B) in vaginal wash were measured by ELISA. FIG. 12C: Two days after rIFN-γ treatment, vaginal tissue sections were stained for VCAM-1+ cells (red) or CD4+ cells (green) and CD31+ cells (green). Blue labelling depicts nuclear staining with DAPI (blue). Images were captured using a ×10 or ×40 objective lens. Scale bars, 100 μm. Data are representative of at least three similar experiments.

FIG. 13A, C57BL/6 mice were immunized intranasally with TK– HSV-2. Six days after challenge of mice immunized 6 weeks previously, neuronal tissue sections (DRG and spinal cord) were stained for CD4+ cells (red) and mouse albumin (green). Blue labelling depicts nuclear staining with DAPI (blue). FIG. 13B, C57BL/6 mice were immunized intranasally with TK– HSV-2. Six weeks later, these mice were challenged with lethal WT HSV-2. Six days after challenge, Oregon green 488-conjugated dextran (70 kDa) (5 mg ml$^{-1}$, 200 μl per mouse) was injected intravenously into intranasally immunized mice. Forty-five minutes later, these mice were killed for immunohistochemical analysis. GM, grey matter; WM, white matter. Data are representative of three similar experiments.

FIG. 14A, C57BL/6 mice were immunized intravenously with WT VSV ($2\times10^6$ plu. per mouse). Five weeks later, these mice were challenged intranasally with WT VSV ($1\times10^7$ p.f.u. per mouse). Six days after challenge, VSV-specific IFN-γ+ CD4$^{30}$ T cells in spleen (CD45.2+) following co-culture with HI-VSV loaded splenocytes (CD45.1+) or HI HSV-2 loaded splenocytes were analysed by flow cytometry. Data are means±s.e.m.

*P<0.05; **P<0.001 (two-tailed unpaired Student's t-test). FIG. 14B and FIG. 14C: Five weeks after VSV immunization, these mice were challenged intranasally with WT VSV ($1\times10^7$ p.f.u. per mouse). Six days after challenge, VSV-specific antibodies and total antibodies in lysate of brain (FIG. 14B) and serum (FIG. 14C) were measured by ELISA. Depletion of CD4 T cells was performed on −4, −1, 2 and 4 days after challenge by intravenous injection of anti-CD4 (GK1.5). FIG. 14D: Albumin levels in tissue homogenates were analysed by ELISA. Data are means±s.e.m. *P<0.05; *P<0.01; ***P<0.001 (Mann-Whitney U-test).

DETAILED DESCRIPTION

Figure 1C:
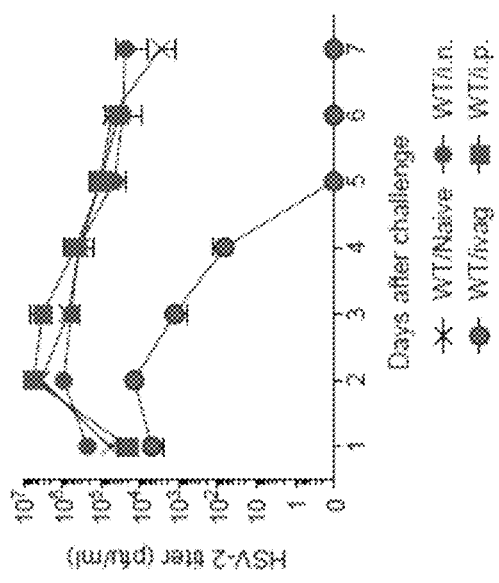
Figure 1B:
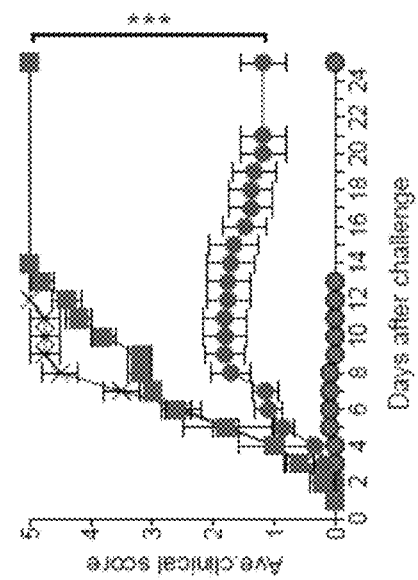
Figure 1A:
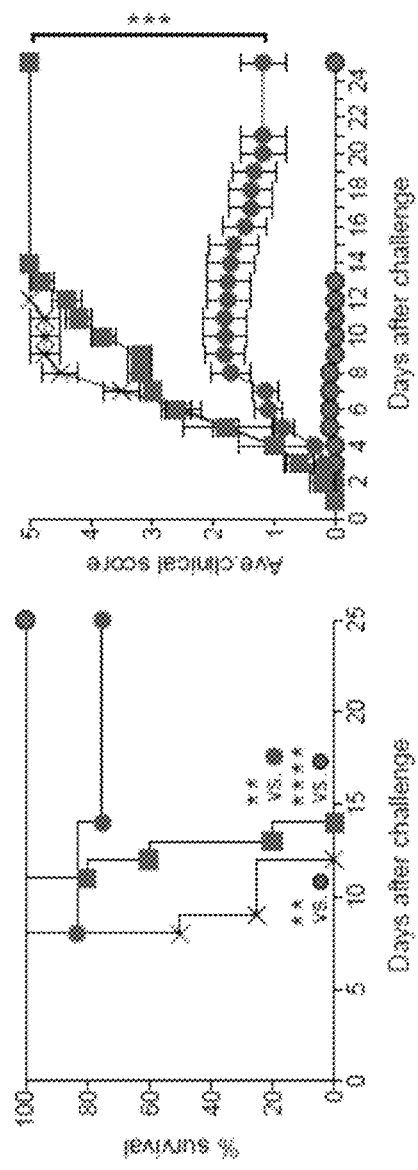

The present invention provides compositions and methods of treating a disease or disorder in immunoprivileged tissue. For example, in some embodiments, the invention provides compositions and methods for treating an infection in immunoprivileged tissue. The present invention relates to inducing a CD4 T cell response, for example a memory CD4 T cell response, in a subject to allow for antibody access in the immunoprivileged tissue.

In one embodiment, the invention provides a composition for treating a disease or disorder comprising (1) an immunogenic agent (e.g., a vaccine) to induce an immune response and (2) a therapeutic antibody or antibody fragment directed to an antigen associated with the disease or disorder. In some embodiments, the immunogenic agent is a vaccine comprising an antigen associated with the disease or disorder. In some embodiments, the antigen of the vaccine is the same as the antigen to which the antibody or antibody fragment is directed. In some embodiments, the antigen of the vaccine is different from the antigen to which the antibody or antibody fragment is directed.

In one embodiment, the composition is useful for treating a pathogenic infection, where the composition comprises (1) an immunogenic agent (e.g., a vaccine) to induce a pathogen-specific immune response and (2) a therapeutic antibody or antibody fragment directed to an antigen of the pathogen. In some embodiments, the immunogenic agent is a vaccine comprising an antigen of the pathogen.

In one embodiment, the composition is useful for treating cancer in the immunoprivileged tissue, where the composition comprises (1) an immunogenic agent (e.g., a vaccine) to induce a tumor-specific immune response and (2) a therapeutic antibody or antibody fragment directed to an antigen associated with the tumor. In some embodiments, the immunogenic agent is a vaccine comprising an antigen associated with the tumor.

In one embodiment, the invention provides a method of treating a disease or disorder in a subject comprising (1) administering to the subject an immunogenic agent to induce an immune response, and (2) administering to the subject a therapeutic antibody or antibody fragment directed to an antigen. In one embodiment, the immunogenic agent is a vaccine comprising an antigen associated with the disease or disorder. The method may be used to treat or prevent a disease or disorder in any immunoprivileged tissue, including but not limited to the brain, spinal cord, peripheral nervous system, testes, eye, placenta, liver, and the like. The method may be used to treat or prevent any disease or disorder of immunoprivileged tissue, including, but not limited to, pathogenic infection, cancer, and neurodegenerative disease, such as Alzheimer's disease.

In one embodiment, the invention provides a method of treating a pathogenic infection in a subject comprising (1) administering to the subject an immunogenic agent to induce a pathogen-specific immune response, and (2) administering to the subject a therapeutic antibody or antibody fragment directed to an antigen of the pathogen. In one embodiment, the immunogenic agent is a vaccine comprising an antigen of the pathogen. The method may be used to treat or prevent any pathogenic infection, including, but not limited to a viral infection, bacterial infection, fungal infection, parasitic infection, helminth infection, protozoan infection, prion infection and the like.

In one embodiment, the invention provides a method of treating cancer in a subject comprising (1) administering to the subject an immunogenic agent to induce a tumor-specific immune response, and (2) administering to the subject a therapeutic antibody or antibody fragment directed to tumor-specific antigen. In one embodiment, the immunogenic agent is a vaccine comprising a tumor-specific antigen.

Definitions

Unless defined otherwise, all technical and scientific terms used herein have the same meaning as commonly understood by one of ordinary skill in the art to which this invention belongs.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%,±5%,±1%, or ±0.1% from the specified value, as such variations are appropriate to perform the disclosed methods.

The term "antibody," as used herein, refers to an immunoglobulin molecule, which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations κ and γ light chains refer to the two major antibody light chain isotypes.

By the term "synthetic antibody" as used herein, is meant an antibody, which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art. The term should also be construed to mean an antibody, which has been generated by the synthesis of an RNA molecule encoding the antibody. The RNA molecule expresses an antibody protein, or an amino acid sequence specifying the antibody, wherein the RNA has been obtained by transcribing DNA (synthetic or cloned) or other technology, which is available and well known in the art.

The term "antigen" or "Ag" as used herein is defined as a molecule that provokes an adaptive immune response. This immune response may involve either antibody production, or the activation of specific immunogenically-competent cells, or both. The skilled artisan will understand that any macromolecule, including virtually all proteins or peptides, can serve as an antigen. Furthermore, antigens can be derived from recombinant or genomic DNA or RNA. A skilled artisan will understand that any DNA or RNA, which comprises a nucleotide sequences or a partial nucleotide sequence encoding a protein that elicits an adaptive immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "adjuvant" as used herein is defined as any molecule to enhance an antigen-specific adaptive immune response.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) RNA, and viruses (e.g., lentiviruses, retroviruses, adenoviruses, and adeno-associated viruses) that incorporate the recombinant polynucleotide.

"Immunogen" refers to any substance introduced into the body in order to generate an immune response. That substance can a physical molecule, such as a protein, or can be encoded by a vector, such as DNA, mRNA, or a virus.

By the term "immune reaction," as used herein, is meant the detectable result of stimulating and/or activating an immune cell.

"Immune response," as the term is used herein, means a process that results in the activation and/or invocation of an effector function in either the T cells, B cells, natural killer (NK) cells, and/or antigen-presenting cells (APCs). Thus, an immune response, as would be understood by the skilled artisan, includes, but is not limited to, any detectable antigen-specific or allogeneic activation of a helper T cell or cytotoxic T cell response, production of antibodies, T cell-mediated activation of allergic reactions, macrophage infiltration, and the like.

"Immune cell," as the term is used herein, means any cell involved in the mounting of an immune response. Such cells include, but are not limited to, T cells, B cells, NK cells, antigen-presenting cells (e.g., dendritic cells and macrophages), monocytes, neutrophils, eosinophils, basophils, and the like.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleosides (nucleobase bound to ribose or deoxyribose sugar via N-glycosidic linkage) are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject.

The terms "patient," "subject," "individual," and the like are used interchangeably herein, and refer to any animal, or cells thereof whether in vitro or in situ, amenable to the methods described herein. In some non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more other species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "therapeutic" as used herein means a treatment and/or prophylaxis. A therapeutic effect is obtained by suppression, diminution, remission, or eradication of at least one sign or symptom of a disease or disorder state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for treating a disease or disorder in an immunoprivileged tissue in a subject in need thereof. The present invention is based in part upon the discovery that memory CD4 T cells are required to allow antibody access to immunoprivileged tissue. For example, it is demonstrated herein that both antibodies and CD4 T cells are required to protect the host after immunization at a distal site. It is shown that memory CD4 T cells migrate to the immunoprivileged tissue, secrete interferon-γ, and mediate local increase in vascular permeability, enabling antibody access. The results reveal a previously unappreciated role of CD4 T cells in mobilizing antibodies to the peripheral sites of infection where they help to limit infection.

The present invention provides a composition for treating or preventing a disease or disorder comprising a first agent and a second agent. In one embodiment, the first agent induces an immune response in the subject. For example, in one embodiment, the first agent induces the activation and production of memory CD4 T cells. In some embodiments, the first agent is an immunogenic composition (e.g., vaccine) that induces an immune response. In one embodiment, the second agent is a therapeutic agent directed to the disease or disorder. For example, in one embodiment, the second agent is an antibody or antibody fragment that specifically binds to an antigen associated with the disease or disorder. The memory CD4 T cells induced by the first agent allows the second agent to access the immunoprivileged tissue.

The present invention provides methods for treating or preventing a disease or disorder of immunoprivileged tissue in a subject in need thereof.

In one embodiment, the method comprises administering to the subject a first agent and a second agent. In one embodiment, the first agent induces an immune response in the subject. For example, in one embodiment, the first agent induces the activation and production of memory CD4 T cells. In some embodiments, the first agent is an immunogenic composition (e.g., vaccine) that induces an immune response. In one embodiment, the second agent is a therapeutic agent directed to the disease or disorder. For example, in one embodiment, the second agent is an antibody or antibody fragment that specifically binds to an antigen associated with the disease or disorder. In one embodiment, the method comprises administering a vaccine to induce an immune response in the subject; and administering a therapeutic antibody or antibody fragment that binds to an antigen associated with the disease or disorder.

In one embodiment, the compositions and methods of the present invention may be used to treat or prevent a disease or disorder in any immunoprivileged tissue, including but not limited to the brain, spinal cord, peripheral nervous system, testes, eye, placenta, liver, and the like.

In one embodiment, the compositions and methods of the present invention may be used to treat or prevent any pathogenic infection, including, but not limited to a viral infection, bacterial infection, fungal infection, parasitic infection, helminth infection and the like.

In one embodiment, the compositions and methods of the present invention may be used to treat or prevent cancer.

In one embodiment, the compositions and methods of the present invention may be used to treat or prevent a neurological disorder, including, but not limited to, Alzheimer's disease.

Compositions

The present invention provides compositions for treating or preventing a disease or disorder comprising a first agent and a second agent. In one embodiment, the first agent induces an immune response in the subject. In some embodiments, the first agent is an immunogenic agent (e.g., vaccine) that induces an immune response.

In one embodiment, the second agent is a therapeutic agent targeted to an antigen associated with the disease or disorder. For example, in one embodiment, the second agent is an antibody or antibody fragment that specifically binds to the antigen.

Immunogenic Agent

In one embodiment, the composition of the present invention comprises an immunogenic agent. In some embodiments, the immunogenic agent comprises a peptide, nucleic acid molecule, cell, or the like, that induces an antigen-specific immune response. For example, in one embodiment, the immunogenic agent comprises an antigen. In some embodiments, the agent is associated with the disease or disorder being treated. In some embodiments, the antigen is associated with the pathogenic infection being treated. In some embodiments, the antigen is a tumor-specific antigen or a tumor-associated antigen.

In some embodiments, the immunogenic agent is a vaccine. For the immunogenic agent to be useful as a vaccine, the immunogenic agent must induce an immune response to the antigen in a cell, tissue or mammal (e.g., a human). In some embodiments, the vaccine induces a protective immune response in the mammal. In one embodiment, the vaccine induces the activation and production of memory CD4 T cells in the mammal. As used herein, an "immunogenic agent" may comprise an antigen (e.g., a peptide or polypeptide), a nucleic acid encoding an antigen (e.g., an antigen expression vector), and a cell expressing or presenting an antigen or cellular component. In some embodiments, the immunogenic agent is an inactivated pathogen, attenuated pathogen, temperature-sensitive pathogen, or the like, which can be used to induce a pathogen-specific immune response.

In some embodiments, the antigen comprises a viral antigen, including but not limited to an antigen of Zika virus, Ebola virus, Japanese encephalitis virus, mumps virus, measles virus, rabies virus, varicella-zoster, Epstein-Barr virus (HHV-4), cytomegalovirus, herpes simplex virus 1 (HSV-1) and herpes simplex virus 2 (HSV-2), human immunodeficiency virus-1 (HIV-1), JC virus, arborviruses, enteroviruses, and West Nile virus, dengue virus, poliovirus, and varicella zoster virus. In some embodiments, the antigen comprises a bacterial antigen, including, but not limited to, an antigen of *Streptococcus pneumoniae, Neisseria meningitides, Streptococcus agalactia*, and *Escherichia coli*. In some embodiments, the antigen comprises a fungal or protozoan antigen, including, but not limited to, an antigen of *Candidiasis, Aspergillosis, Cryptococcosis*, and *Toxoplasma gondii*.

In some embodiments, the antigen comprises a tumor-specific antigen or a tumor-associated antigen, including but not limited to: differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, Aim2, Art-4, EphA2, EZH2, Fosll, PTH-rP, Sox11, Whsc2, YKL-40 and TPS.

In some embodiments, the antigen comprises an antigen associated with a neurological disorder. Exemplary antigens associated with a neurological disorder include, but are not limited to various monomeric and aggregated forms of Aβ, tau, BACE1, α-synuclein, huntingtin, TAR-DNA binding protein 43 kDA, superoxide dismutase 1, prion protein, and fragments thereof.

In particular embodiments the immunogenic agent comprises or encodes all or part of any antigen described herein, or an immunologically functional equivalent thereof. In other embodiments, the immunogenic agent is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In some embodiments, the immunogenic agent is conjugated to or comprises an HLA anchor motif amino acids. In some instances, the immunogenic agent of the invention can be used to induce an antigen-specific immune response, including the production of memory CD4 T cells, in the subject.

A vaccine of the present invention may vary in its composition of peptides, nucleic acids and/or cellular components. In a non-limiting example, an antigen might also be formulated with an adjuvant. Of course, it will be understood that various compositions described herein may further comprise additional components. For example, one or more vaccine components may be comprised in a lipid or liposome. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

Exemplary adjuvants include, but are not limited to, alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MEW, CD80, CD86 including IL-15 having the signal sequence deleted and optionally including the signal peptide from IgE. Other genes which may be useful adjuvants include those encoding: MCP-I, MIP-Ia, MIP-Ip, IL-8, RANTES, L-selectin, P-selectin, E-selectin, CD34, Gly-CAM-1, MadCAM-1, LFA-I, VLA-I, Mac-1, p150.95, PECAM, ICAM-I, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Fit, Apo-1, p55, WSL-I, DR3, TRAMP, Apo-3, AIR, LARD, NGRF, DR4, DR5, KILLER, TRAIL-R2, TRICK2, DR6, Caspase ICE, Fos, c-jun, Sp-I, Ap-I, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP 1, TAP2, anti-CTLA4-sc, anti-LAG3-Ig, anti-TIM3-Ig and functional fragments thereof.

In one embodiment, the peptide vaccine of the invention includes, but is not limited to a peptide mixed with adjuvant substances and a peptide which is introduced together with an APC. The most common cells used for the latter type of vaccine are bone marrow and peripheral blood derived dendritic cells, as these cells express costimulatory molecules that help activation of T cells. WO00/06723 discloses a cellular vaccine composition which includes an APC presenting tumor associated antigen peptides. Presenting the peptide can be effected by loading the APC with a polynucleotide (e.g., DNA, RNA, etc.) encoding the peptide or loading the APC with the peptide itself.

When an immunogenic agent induces an anti-pathogen immune response upon inoculation into an animal, the immunogenic agent is decided to have anti-pathogen immunity inducing effect. The pathogen-specific immune response can be detected by observing in vivo or in vitro the response of the immune system in the host against the peptide.

For example, a method for detecting the induction of cytotoxic T lymphocytes is well known. A foreign substance that enters the living body is presented to T cells and B cells by the action of APCs. T cells that respond to the antigen presented by APC in an antigen specific manner differentiate into cytotoxic T cells (also referred to as cytotoxic T lymphocytes or CTLs) due to stimulation by the antigen. These antigen stimulated cells then proliferate. This process is referred to herein as "activation" of T cells. Therefore, CTL induction by a certain peptide or combination of peptides of the invention can be evaluated by presenting the peptide to a T cell by APC, and detecting the induction of CTL. Furthermore, APCs have the effect of activating CD4+ T cells, CD8+T cells, macrophages, eosinophils and NK cells.

A method for evaluating the inducing action of CTL using dendritic cells (DCs) as APC is well known in the art. DC is a representative APC having the strongest CTL inducing action among APCs. In this method, the peptide or combination of peptides are initially contacted with DC and then this DC is contacted with T cells. Detection of T cells having cytotoxic effects against the cells of interest after the contact with DC shows that the peptide or combination of peptides have an activity of inducing the cytotoxic T cells. Furthermore, the induced immune response can be also examined by measuring IFN-gamma produced and released by CTL in the presence of antigen-presenting cells that carry immobilized peptide or combination of peptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The induction of a pathogen-specific immune response can be further confirmed by observing the induction of antibody production against the specific pathogen. In one embodiment, the induction of a pathogen-specific immune response can be further confirmed by observing the activation and production of memory CD4 T cells.

Therapeutic Agent

In one embodiment, the composition comprises a therapeutic agent. In some embodiments, the therapeutic agent comprises a peptide, nucleic acid molecule, small molecule, antibody, or the like. In some embodiments, the therapeutic agent is targeted to a site of disease or infection in the immunoprivileged tissue. In some embodiments, the therapeutic agent is targeted to the pathogen of the infected immunoprivileged tissue. For example, in some embodiments, the therapeutic agent comprises an antibody or antibody fragment that binds to the pathogen or antigen of the pathogen. In some embodiments, the therapeutic agent comprises an antibody or antibody fragment that binds to a tumor-specific antigen or tumor-associated antigen. In some embodiments, the therapeutic agent comprises an antibody or antibody fragment that binds to an antigen associated with a neurological disease.

In one embodiment, the therapeutic agent comprises a therapeutic antibody or antibody fragment. The therapeutic antibody or antibody fragment includes any antibody known in the art which binds the pathogen, induces the killing of the pathogen, reduces pathogenic infection, or prevents spread of the pathogenic infection. The therapeutic antibody or antibody fragment includes any antibody known in the art which binds to a tumor cell, induces the killing of the tumor cell, or prevents tumor cell proliferation or metastasis. In some embodiments, the therapeutic agent comprises a T-cell that has been modified to express an antibody or antibody fragment (e.g., chimeric antigen receptor T-cell). In one embodiment, the therapeutic agent comprises an antibody-drug conjugate.

In some embodiments, the therapeutic antibody or antibody fragment binds to the same antigen of the immunogenic agent. In some embodiments, the antigen to which therapeutic antibody or antibody fragment binds to a different from the antigen of the immunogenic agent. In some embodiments, the antigen to which the therapeutic agent binds and the antigen of the immunogenic agent are each associated with the same disease, disorder, or infection.

Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, bind to the specific antigens of interest, and they are able to bind the antigen present on Western blots, in solution in enzyme linked immunoassays, in fluorescence activated cells sorting (FACS) assays, in magenetic-actived cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

The invention also includes functional equivalents of the antibodies described herein. Functional equivalents have binding characteristics comparable to those of the antibodies, and include, for example, hybridized and single chain antibodies, as well as fragments thereof. Methods of producing such functional equivalents are disclosed in PCT Application WO 93/21319 and PCT Application WO 89/09622.

Functional equivalents include polypeptides with amino acid sequences substantially the same as the amino acid sequence of the variable or hypervariable regions of the antibodies. "Substantially the same" amino acid sequence is defined herein as a sequence with at least 70%, at least about 80%, at least about 90%, at least about 95%, or at least 99% homology to another amino acid sequence (or any integer in between 70 and 99), as determined by the FASTA search method in accordance with Pearson and Lipman, 1988 *Proc. Nat'l. Acad. Sci. USA* 85: 2444-2448. Chimeric or other hybrid antibodies have constant regions derived substantially or exclusively from human antibody constant regions and variable regions derived substantially or exclusively from the sequence of the variable region of a monoclonal antibody from each stable hybridoma.

Single chain antibodies (scFv) or Fv fragments are polypeptides that consist of the variable region of the heavy chain of the antibody linked to the variable region of the light chain, with or without an interconnecting linker. Thus, the Fv comprises an antibody combining site.

Functional equivalents of the antibodies of the invention further include fragments of antibodies that have the same, or substantially the same, binding characteristics to those of the whole antibody. Such fragments may contain one or both Fab fragments or the F(ab')$_2$ fragment. The antibody fragments contain all six complement determining regions of the whole antibody, although fragments containing fewer than all of such regions, such as three, four or five complement determining regions, are also functional. The functional equivalents are members of the IgG immunoglobulin class and subclasses thereof, but may be or may combine with any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, hybrid antibodies with desired effector function are produced. Exemplary constant regions are gamma 1 (IgG1), gamma 2 (IgG2), gamma 3 (IgG3), and gamma 4 (IgG4). The light chain constant region can be of the kappa or lambda type.

The immunoglobulins of the present invention can be monovalent, divalent or polyvalent. Monovalent immunoglobulins are dimers (HL) formed of a hybrid heavy chain associated through disulfide bridges with a hybrid light chain. Divalent immunoglobulins are tetramers ($H_2L_2$) formed of two dimers associated through at least one disulfide bridge.

Methods

The invention provides a method for treating, or preventing infection disease or disorder of immunoprivileged tissue. The therapeutic compounds or compositions of the invention may be administered prophylactically or therapeutically to subjects suffering from or at risk of (or susceptible to) developing the disease or disorder. Such subjects may be identified using standard clinical methods. In the context of the present invention, prophylactic administration occurs prior to the manifestation of overt clinical symptoms, such that an infection is prevented or alternatively delayed in its progression. In the context of the field of medicine, the term "prevent" encompasses any activity which reduces the burden of mortality or morbidity from the disease or disorder. Prevention can occur at primary, secondary and tertiary prevention levels. While primary prevention avoids the development of a disease, secondary and tertiary levels of prevention encompass activities aimed at preventing the progression of an infection and the emergence of symptoms as well as reducing the negative impact of an already established disease by restoring function and reducing disease or disorder-related complications.

In one embodiment, the method comprises administering to the subject an immunogenic agent (e.g., a vaccine), as described elsewhere herein. In one embodiment, the immunogenic agent comprises an adjuvant. An adjuvant refers to a compound that enhances the immune response against the peptide or combination of peptides when administered together (or successively) with the peptide having immunological activity. Examples of suitable adjuvants include cholera toxin, salmonella toxin, alum and such, but are not limited thereto. Furthermore, a vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

When using cells of the invention (e.g., peptide-load antigen presenting cell or peptide-specific IFNγ-secreting CD4+ T cells) as the vaccine, the disease or disorder may be treated or prevent, for example, by the ex vivo method. For example, PBMCs of the subject receiving treatment or prevention are collected, contacted ex vivo with an antigen or nucleic acid encoding an antigen. Following the induction of peptide-load antigen presenting cells or peptide-specific IFNγ-secreting CD4+ T cells, the cells may be administered to the subject. The cells can be induced by introducing a vector encoding the peptide or combination of peptides into them ex vivo. The cells induced in vitro can be cloned prior to administration. By cloning and growing cells having high activity of damaging target cells, cellular immunotherapy can be performed more effectively. Furthermore, cells of the invention isolated in this manner may be used for cellular immunotherapy not only against individuals from whom the cells are derived, but also against similar types of diseases in other individuals.

In one embodiment, the method comprises administering to the subject a therapeutic agent, as described elsewhere herein. For example, in one embodiment, the method comprises administering a therapeutic antibody or antibody fragment that binds to an antigen.

The different agents may be administered to the subject in any order and in any suitable interval. For example, in some embodiments, the immunogenic agent and the therapeutic agent are administered simultaneously or near simultaneously. In some embodiments, the method comprises a staggered administration of the agents, where the immunogenic agent is administered and the therapeutic agent is administered at some later time point. In some embodiments, the method comprises a staggered administration of the agents, where the therapeutic agent is administered and the immunogenic agent is administered at some later time point. Any suitable interval of administration which produces the desired therapeutic effect may be used.

The method of the present invention may be used to treat any pathogenic infection of immunoprivileged tissue. The method may be used to treat or prevent a pathogenic infection in any immunoprivileged tissue, including but not limited to the brain, spinal cord, peripheral nervous system, testes, eye, placenta, liver, and the like. For example, the method may be used to treat or prevent infections caused by a virus, a fungus, a protozoan, a parasite, an arthropod, a prion, a mycobacterium, or a bacterium, including a bacterium that has developed resistance to one or more antibiotics. Exemplary viral infections treated or prevented by way of the present method include, but is not limited to infections caused by Zika virus, ebola virus, Japanese encephalitis virus, mumps virus, measles virus, rabies virus, varicella-zoster, Epstein-Barr virus (HHV-4), cytomegalovirus, herpes simplex virus 1 (HSV-1) and herpes simplex virus 2 (HSV-2), human immunodeficiency virus-1 (HIV-1), JC virus, arborviruses, enteroviruses, and West Nile virus, dengue virus, poliovirus, and varicella zoster virus. Exemplary bacterial infections treated or prevented by way of the present method include, but is not limited to infections caused by *Streptococcus pneumoniae, Neisseria meningitides, Streptococcus agalactia*, and *Escherichia coli*. Exemplary fungal or protozoan infections treated or prevented by way of the present method include, but is not limited to infections caused by *Candidiasis, Aspergillosis, Cryptococcosis*, and *Toxoplasma gondii*.

In some embodiments, the present invention provides a method for treating or preventing a disease or disorder associated with infection of immunoprivileged tissue, including but not limited to meningitis, encephalitis, meningoencephalitis, epidural abscess, subdural abscess, brain abscess, and progressive multifocal leukoencephalopathy (PML).

The method of the present invention may be used to treat or prevent cancer. The method may be used to reduce tumor growth, proliferation, or metastasis in any immunoprivileged tissue, including but not limited to the brain, spinal cord, peripheral nervous system, testes, eye, placenta, liver, and the like. Exemplary forms of cancer treated or prevented by way of the present invention, include, but is not limited to glioblastoma, meningioma, acoustic neuroma, astrocytoma, chordoma, CNS lymphoma, craniopharyngioma, brain stem glioma, ependymoma, mixed glioma, optic nerve glioma, supependymoma, medullablastoma, meningioma, metastatic brain tumors, .oligodendroglioma, pituitary tumors, primitive neuroectodermal, schwannoma, juvenile pilocytic astrocytoma, pineal tumor, rhaboid tumor, spinal cancer, spinal cord tumor, testicular cancer, intraocular melanoma, and liver cancer, hepatocellular cancer, bile duct cancer, and hepatoblastoma.

The method of the present invention may be used to treat or prevent a neurological disorder. Exemplary neurological disorders treated or prevented by way of the present invention, include, but is not limited to Alzheimer's disease, Parkinson's disease, tauopathy, frontotemporal dementia, Huntington's disease, and prion disease.

The treatment and prophylactic methods of the invention may be used to treat or prevent a disease or disorder of immunoprivileged tissue in any subject in need. For example, in some embodiments, the subject includes, but is not limited to humans and other primates and mammals including commercially relevant mammals such as non-human primates, cattle, pigs, horses, sheep, cats, dogs, rats, and mice.

In some embodiments, the method comprises further administering an additional therapeutic agent, including, but not limited to, an antibiotic, antiviral agent, antifungal agent, and anti-inflammatory agent. In one embodiment, the antibiotic is selected from Amoxicillin, Ampicillin, Cloxacillin, Dicloxacillin, Nafcillin, Oxacillin, Penicillin G, Penicillin V, Piperacillin, Cefadroxil (cefadroxyl), Cefalexin (cephalexin), Cefalotin (cephalothin), Cefapirin (cephapirin), Cefazolin (cephazolin), Cefradine (cephradine), Cefaclor, Cefotetan, Cefoxitin, Cefprozil (cefproxil), Cefuroxime, Cefdinir, Cefixime, Cefotaxime, Cefpodoxime, Ceftizoxime, Ceftriaxone, Ceftazidime, Cefepime, Ceftobiprole, Ceftaroline, Aztreonam, Imipenem, Imipenem, cilastatin, Doripenem, Meropenem, Ertapenem, Azithromycin, Erythromycin, Clarithromycin, Dirithromycin, Roxithromycin, Clindamycin, Lincomycin, Amikacin, Gentamicin, Tobramycin, Ciprofloxacin, Levofloxacin, Moxifloxacin, Trimethoprim-Sulfamethoxazole, Doxycycline, Tetracycline, Vancomycin, Teicoplanin, Telavancin, and Linezolid. Exemplary antiviral agents that can be used with the methods of the invention include, but are not limited to, Abacavir, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Interferon type III, Interferon type II, Interferon type I, Interferon, Lamivudine, Lopinavir, Loviride, Maraviroc, Moroxydine, Methisazone, Nelfinavir, Nevirapine, Nexavir, Nitazoxanide, Novir, Peginterferon alfa-2a, Penciclovir, Peramivir, Pleconaril, Podophyllotoxin, Raltegravir, Ribavirin, Rimantadine, Ritonavir, Pyramidine, Saquinavir, Sofosbuvir, Stavudine, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, and Zidovudine. Non-limiting examples of anti-inflammatory agents include non-steroidal anti-inflammatory drugs (NSAIDs), steroidal anti-inflammatory drugs, beta-agonists, anticholingeric agents, and methyl xanthines. Examples of NSAIDs include, but are not limited to, aspirin, ibuprofen, celecoxib, diclofenac, etodolac, fenoprofen, indomethacin, ketoralac, oxaprozin, nabumentone, sulindac, tolmentin, rofecoxib, naproxen, ketoprofen, nabumetone, diclofenac & misoprostol, ibuprofen, ketorolac, valdecoxib, meloxicam, flurbiprofen, and piroxicam. Such NSAIDs function by inhibiting a cyclooxygenase enzyme (e.g., COX-1 and/or COX-2). Examples of steroidal anti-inflammatory drugs include, but are not limited to, glucocorticoids, dexamethasone, cortisone, hydrocortisone, prednisone, prednisolone, triamcinolone, azulfidine, and eicosanoids such as prostaglandins, thromboxanes, and leukotrienes.

In some embodiments, the method comprises further administering an additional anti-cancer treatment modality including, but not limited to, chemotherapy, radiation, surgery, hormonal therapy, or a combination thereof.

Pharmaceutical

The therapeutic and prophylactic methods of the invention thus encompass the use of pharmaceutical compositions. The pharmaceutical compositions useful for practicing the invention may be administered to deliver a dose of between 1 ng/kg/day and 100 mg/kg/day. In one embodiment, the invention envisions administration of a dose which results in a concentration of the compound of the present invention between 1 µM and 10 µM in a mammal.

Typically, dosages which may be administered in a method of the invention to an animal that ranges in amount from 0.5 µg to about 50 mg per kilogram of body weight of the animal. While the precise dosage administered will vary depending upon any number of factors, including but not limited to, the type of animal and type of disease state being treated, the age of the animal and the route of administration. In one embodiment, the dosage of the compound will vary from about 1 µg to about 10 mg per kilogram of body weight of the animal. In one embodiment, the dosage will vary from about 3 µg to about 1 mg per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Other active agents useful in the treatment of fibrosis include anti-inflammatories, including corticosteroids, and immunosuppressants.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, or about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. In one embodiment, such powders comprise particles wherein at least 98% of the particles by weight have a diameter greater than 0.5 nanometers and at least 95% of the particles by number have a diameter less than 7 nanometers. In one embodiment, at least 95% of the particles by weight have a diameter greater than 1 nanometer and at least 90% of the particles by number have a diameter less than 6 nanometers. In some instances dry powder compositions include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (in some instances having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. In one embodiment, the droplets provided by this route of administration have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. In one embodiment, such powdered, aerosolized, or aerosolized formulations, when dispersed, have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples are not to be construed as limiting in any way the remainder of the disclosure.

Example 1

The materials and methods employed in these experiments are now described.

Mice

Six- to eight-week-old female C57BL/6 (CD45.2$^+$) and congenic C57BL/6 B6.SJL-PtprcaPep3b/BoyJ (B6.Ly5.1) (CD45.1$^+$) mice, B6.129S2-Igh$^{tm1Cgn}$/J (μMT) mice, anti-HEL B-cell receptor (BCR)-transgenic C57BL/6-TgN (Ig-helMD4) (HELTg) mice, CBy.PL (B6)-Thy1$^a$/ScrJ (Thy1.1$^+$ BALB/c) mice and B6.129X1-Fcgrt$^{tm1Dcr}$/DcrJ (FcRn$^{-/-}$) mice were purchased from the National Cancer Institute and Jackson Laboratory. J$_H$D mice (B-cell deficient on BALB/c background) were obtained from Taconic Animal Models.

Viruses

HSV-2 strains 186syn$^-$ TK$^-$ and 186syn$^-$ were obtained. These viruses were propagated and titerd on Vero cells (ATCC CCL-81) as previously described (Laidlaw, B. J. et al., 2014, Immunity 41, 633-645). Influenza virus A/Puerto Rico/3/334 (A/PR8: H1N1) and WT/VSV were propagated as previously described (Laidlaw, B. J. et al., 2014, Immunity 41, 633-645, Sasai, M., et al., 2010, Science 329, 1530-1534).

Virus Infection

Six- to eight-week-old female mice injected subcutaneously with Depo Provera (Pharmacia Upjohn, 2 mg per mouse) were immunized intravaginally, intraperitoneally or intranasally with 10$^5$ p.f.u. of HSV-2 (186syn–TK–) as previously described (Iijima, N. et al., 2014, Science 346, 93-98). For secondary challenge, immunized mice were challenged vaginally with 10$^4$ p.f.u. of WT HSV-2 (186syn$^-$) (100% lethal dose for naive mice). In the case of BALB/c and J$_H$D mice, these mice were immunized with 5×10$^4$ to 10$^5$ p.f.u. of HSV-2. For secondary challenge, immunized mice were challenged with 10$^5$ p.f.u. of WT HSV-2 (100% lethal dose for naive mice). The severity of disease was scored as follows: 0, no sign; 1, slight genital erythema and oedema; 2, moderate genital inflammation; 3, purulent genital lesions; 4, hind-limb paralysis; 5, pre-moribund (Laidlaw, B. J. et al., 2014, Immunity 41, 633-645). Owing to humane concerns, the animals were euthanized before reaching moribund state. To measure virus titer in peripheral tissues, vaginal tissues, DRG and spinal cord were harvested in ABC buffer (0.5 mM MgCl$_2$6H$_2$O, 0.9 mM CaCl$_2$2H$_2$O, 1% glucose, 5% HI FBS and penicillin-streptomycin) including 1% amphotericin-B (Sigma). Thereafter, these tissues were homogenized by lysing matrix D (MP Biomedicals), followed by clarifying by centrifugation. Viral titers were obtained by titration of tissue samples on a Vero cell monolayer. Protein concentration in tissue homogenates was measured by a DC protein assay kit (Bio-Rad Laboratories). C57BL/6 mice were immunized intravenously with WT/VSV (2×10$^6$ p.f.u. per mouse) or intranasally with influenza A/PR8 (10 p.f.u. per mouse). For secondary challenge, VSV-immunized mice were re-infected intranasally with WT/VSV (1×10$^7$ p.f.u. per mouse).

Antibodies

Anti-CD90.2 (30-H12), anti-CD90.1 (OX-7), anti-CD45.2 (104), anti-CD45.1 (A20), anti-CD4 (GK1.5, RM4-5 and RM4-4), anti-CD19 (6D5), anti-CD45R/B220 (RA3-6B2), anti-MHC class II (I-A/I-E, M5/114.15.2), anti-CD69 (H1.2F3), anti-CD44 (IM7), anti-CD49d (R1-2), anti-NKp46 (29A1.4) and anti-IFN-γ (XMG1.2 and R4-6A2) were purchased from e-Bioscience or Biolegend.

Isolation of Leukocytes from Peripheral Tissues

The genital tracts of vaginal tissues treated with Depo-Provera were dissected from the urethra and cervix. Before collection of neuronal tissues, mice were perfused extensively using transcardiac perfusion and perfusion through inferior vena cava and great saphenous vein with more than 30 ml of PBS. The DRG and the adjacent region of the spinal cord were harvested in PBS for flow cytometry or ABC buffer for tissue homogenization. The tissues in PBS were then incubated with 0.5 mg ml$^{-1}$ Dispase II (Roche) for 15 min at 37° C. Thereafter, vaginal tissues were digested with 1 mg ml$^{-1}$ collagenase D (Roche) and 30 μg ml$^{-1}$ DNase I (Sigma-Aldrich) at 37° C. for 25 min. The resulting cells were filtered through a 70-μm filter (Iijima, N. et al., 2011, Proc. Natl Acad. Sci. USA 108, 284-289), Johnson, A. J. et al., 2008, J. Virol. 82, 9678-9688).

Flow Cytometry

Preparation of single-cell suspensions from spleen, draining lymph nodes (inguinal lymph node and iliac lymph nodes), vagina and neuronal tissues were described previously. Multiparameter analyses were performed on an LSR II flow cytometer (Becton Dickinson) and analyzed using FlowJo software (Tree Star). To detect HSV-2-speific CD4$^+$ T cells or VSV-specific CD4$^+$ T cells (CD45.1$^+$ or CD45.2$^+$), single-cell suspensions from vaginal tissues of TK$^-$ HSV-2-immunized mice or VSV immunized mice were stimulated in the presence of 5 μg ml$^{-1}$ Brefeldin A with naive splenocytes (CD45.1$^+$CD45.2$^+$) loaded with heat-inactivated HSV-2 antigen, heat-inactivated WT VSV and heat-inactivated influenza virus A/PR8 for around 12 h (Iijima, N. et al., 2014, Science 346, 93-98). To detect HSV-2-specific CD4$^+$ T cells in BALB/c and J$_H$D mice, single-cell suspensions (CD90.2$^+$) from vaginal tissues of TK$^-$ HSV-2-immunized mice were stimulated with naive splenocytes (CD90.1$^+$) loaded with heat-inactivated HSV-2 antigen.

In Vivo Treatment with Neutralizing/Depleting Antibodies

C57BL/6 mice or BALB/c mice were immunized with TK$^-$ HSV-2 virus. Five to eight weeks later, these mice were injected intravenously (tail vain) with 300 μg of anti-CD4 (GK1.5; BioXCell) or anti-IFN-γ (XMG1.2; BioXCell) antibody at days -4, -1, 2 and 4 after HSV-2 challenge. In vivo depletion for CD4 was confirmed by fluorescence-activated cell sorting analysis of the cell suspension from spleen. For the neutralization of α4-integrin, purified anti-mouse α4 integrin/CD49d (PS/2; SouthernBiotech) was given a tail vain injection of 300 μg antibody at days 2 and 4 after challenge.

Parabiosis

Parabiosis was performed as previously described with slight modifications (Iijima et al., 2014, Science, 346: 93-98). Naive or immunized C57BL/6 mice, HELTg and μMT mice were anaesthetized with a mixture of ketamine/xylazine (100 mg/kg and 10 mg/kg body weight respectively). After shaving the corresponding lateral aspects of each mouse, matching skin incisions were made from behind the ear to hip and sutured together with Chromic Gut (4-0, Henry Schein) absorbable suture, then these areas were clipped with 7-mm stainless-steel wound clips (Roboz).

Measurement of Virus-Specific Ig and Total Ig in Serum and Tissue Homogenates

Ninety-six-well EIA/RIA plates were filled with 100 μl of heat-inactivated purified HSV-2 (10$^4$-10$^5$ p.f.u. equivalent per 100 μl) or heat-inactivated purified VSV (5×10$^5$ p.f.u. equivalent per 100 μl) for virus-specific Ig measurement or goat anti-mouse Ig (1:1,000; SouthernBiotech, 1010-01) for total Ig measurement in carbonate buffer (pH 9.5) and then incubated overnight at 4° C. On the following day, these plates were washed with PBS-Tween 20 and blocked for 2 h with 5% FBS in PBS. Tissue samples and serum samples in ABC buffer were then plated in the wells and incubated for at least 4 h at ambient temperature. After washing in PBS-Tween 20, HRP-conjugated anti-mouse IgG1, IgG3, IgM, IgA, IgG2a, IgG2b or IgG2c (SouthernBiotech) was added to the wells for 1 h, followed by washing and adding TMB solution (eBioscience). Reactions were stopped with 1 N $H_2SO_4$ and absorbance was measured at 450 nm. The sample antibody titers were defined by using Ig standard (C57BL/6 Mouse Immunoglobulin Panel; SouthernBiotech) or mouse IgG2a (HOPC-1; SouthernBiotech).

Albumin ELISA

Using tissue homogenates (DRG and spinal cord) prepared after extensive perfusion, albumin ELISA (Genway) was performed according to instruction.

Immunofluorescence staining

Frozen sections 8 μm in thickness were cut, fixed and left to dry at ambient temperature. These tissues were stained with the antibodies (anti-CD4 (H129.19), anti-MHC class II (M5/114.15.2) anti-VCAM-1 (429/MVCAM.A), anti-CD31 (390 and MEC13.3), anti-Ly6G (1A8), anti-CD11b (M1/70) and anti-mouse albumin (Goat pAb/Bethyl Laboratories)) as previously described (Iijima, N. et al., 2014, Science 346, 93-98). These slides were washed and incubated with DAPI and mounted with Fluoromount-G (SouthernBiotech). They were analyzed by fluorescence microscopy (BX51; Olympus).

Vascular Permeability Assays

Spinal column was harvested from intranasal TK⁻ HSV-2-immunized mice 45 min after tail vein injection with 200 μl of 5 mg ml⁻¹ Oregon Green 488-conjugated dextran (70 kDa, D7173, Thermo Fisher Scientific) in PBS. Spine was then fixed with 4% paraformaldehyde in PBS overnight, and frozen sections cut (8 μm in thickness) for immunohistochemical analysis (Knowland, D. et al., 2014, Neuron 82, 603-617).

DNA Isolation from Tissues

C57BL/6 mice were immunized intranasally with TK⁻ HSV-2. Six weeks later, vaginal tissues, DRG and spinal cord of these mice were lysed in 10 mg ml⁻¹ Proteinase K (Roche) to isolate DNA at 55° C. overnight. After removing these tubes, phenol equilibrated with Tris pH 8.0 was added. Thereafter, upper aqueous phase was added to phenol/chloroform (1:1). The upper aqueous phase was re-suspended with sodium acetate, pH 6.0, and 100% ethanol at room temperature. After shaking and centrifuging, the concentration of isolated DNA pellet was measured. The level of HSV-2 genomic DNA in peripheral tissues on the basis of HSV-2 gD (forward primer: AGCGAGGATAACCTGG-GATT (SEQ ID NO: 1); reverse primer: GGGA-TAAAGCGGGGTAACAT (SEQ ID NO: 2)) was analyzed by quantitative PCR using purified viral DNA genome as standard.

Statistical Analysis

Survival curves were analyzed using a log-rank test. For other data, normally distributed continuous variable comparisons used a two-tailed unpaired Student's t-test or paired Student's t-test with Prism software. To compare two non-parametric data sets, a Mann-Whitney U-test was used.

The results of the experiments are now described.

Figure 1D:
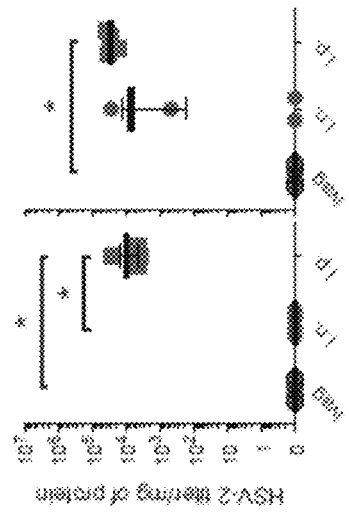
Figure 5A:
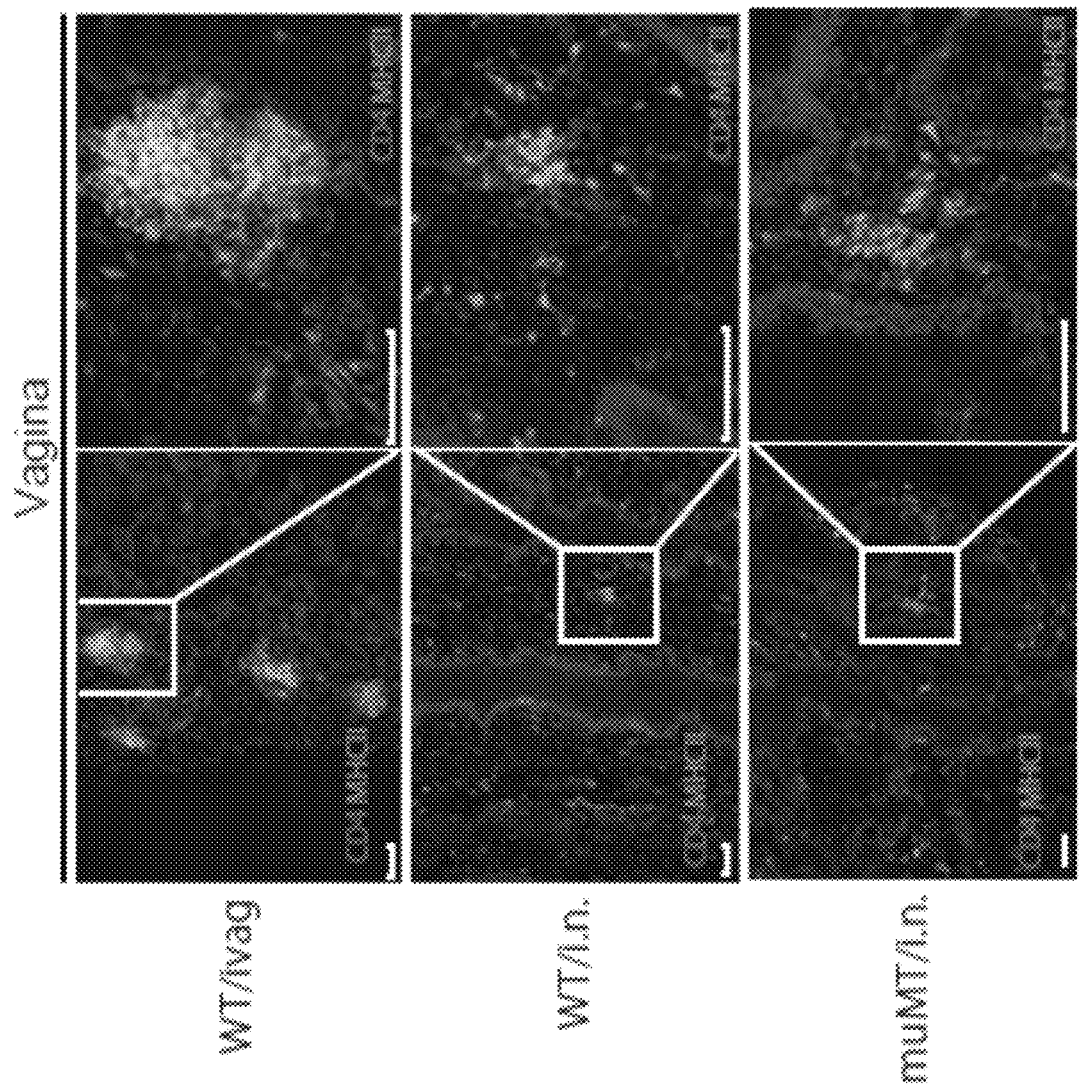
Figure 5B:
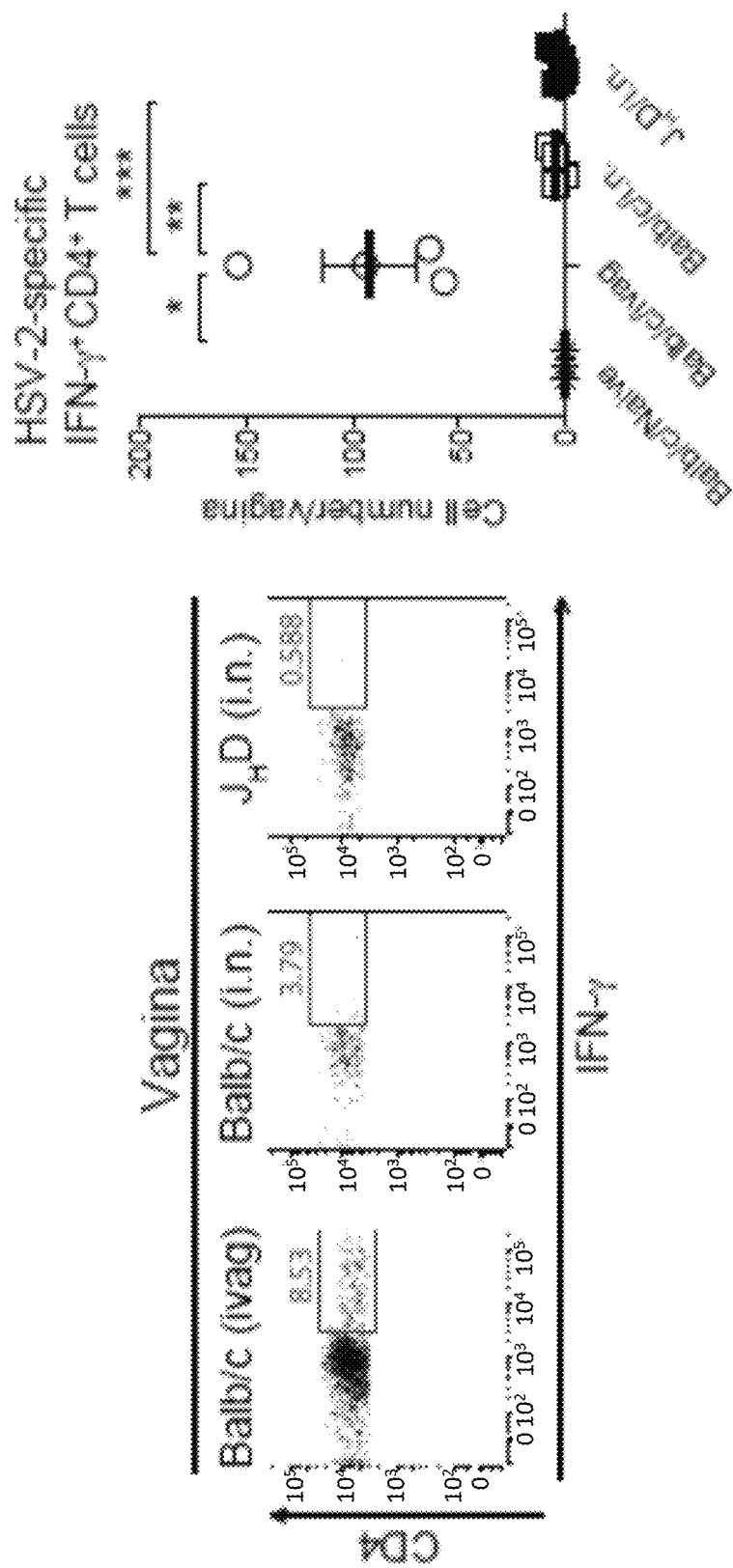
Figure 5C:
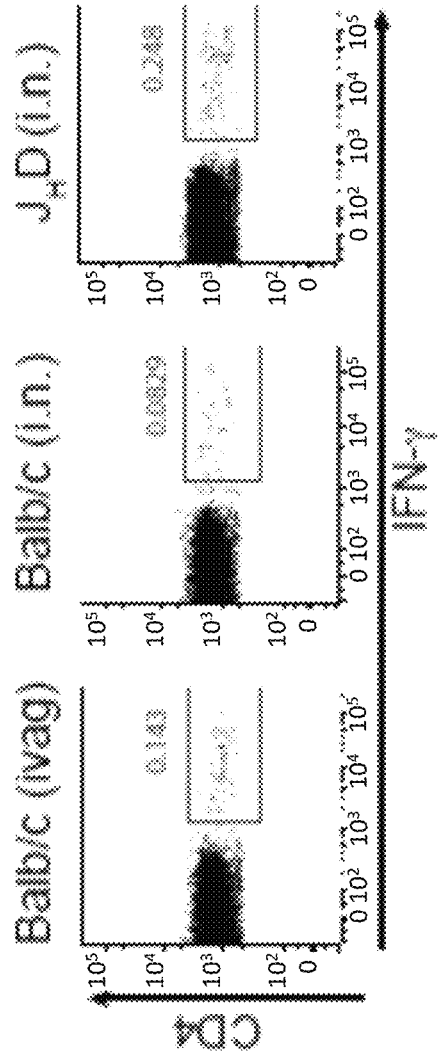
Figure 5D:
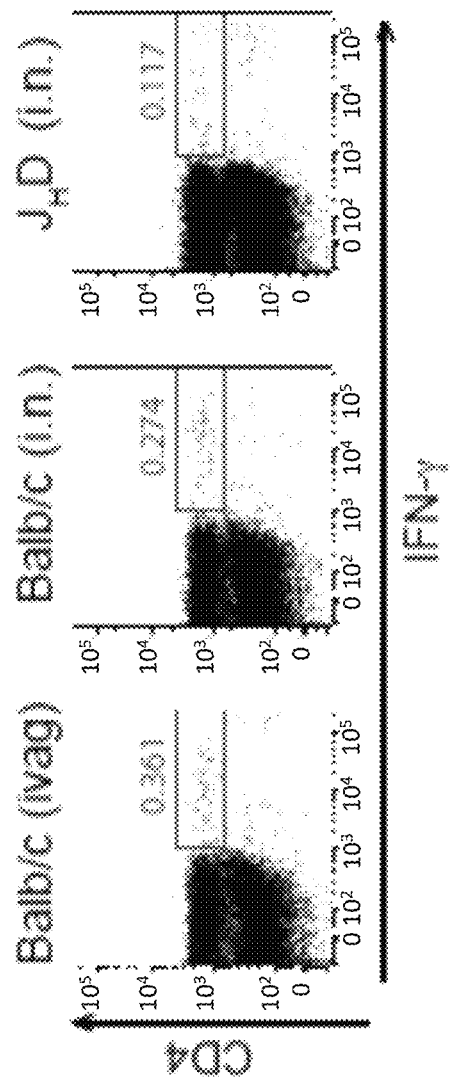

To investigate the mechanism of antibody-mediated protection within the barrier-protected tissues, a mouse model of genital herpes infection was used. Herpes simplex virus type 2 (HSV-2) enters the host through the mucosal epithelia, and infects the innervating neurons in the dorsal root ganglia (DRG) to establish latency (Koelle, D. M. et al., 2008, Annu. Rev. Med. 59, 381-395, Knipe, D. M. et al., 2008 Nature Rev. Microbiol. 6, 211-221). Vaginal immunization by an attenuated HSV-2 with deletion of the thymidine kinase gene (TK⁻ HSV-2) provides complete protection from lethal disease following genital challenge with wild-type (WT) HSV-2 (Parr, M. B. et al., 1994, Lab. Invest. 70, 369-380) by establishing tissue-resident memory T cells (TRM) (Iijima, N. et al., 2014, Science 346, 93-98). In vaginally immunized mice, interferon (IFN)-γ-secretion by CD4 T cells, but not antibodies, are required for protection (Milligan, G. N. et al., 1998, J. Immunol. 160, 6093-6100, Parr, M. B. et al., 2000, Immunology 101, 126-131). In contrast, distal immunization with the same virus fails to establish TRM and provides only partial protection (Iijima, N. et al., 2014, 2014, Science 346, 93-98). Nevertheless, of the distal immunization routes tested, intranasal immunization with TK⁻ HSV-2 provided the most robust protection against intravaginal challenge with WT HSV-2, whereas intraperitoneal immunization provided the least protection (FIG. 1A through FIG. 1D) Sato, A. et al., 2014, J. Virol. 88, 13699-13708, Jones, C. A. et al., 2000, Virology 278, 137-150). As shown previously (Iijima, N. et al., 2014, Science 346, 93-98), intransal immunization did not establish TRM in the genital mucosa (FIG. 5A, FIG. 5B), despite generating a comparable circulating memory T-cell pool (FIG. 5C, FIG. 5D). After vaginal HSV-2 challenge, mice that were immunized intranasally with TK– HSV-2 were unable to control viral replication within the vaginal mucosa (FIG. 1C), but had significantly reduced viral replication in the innervating neurons of the DRG (FIG. 1D). Notably, it was found that protection conferred by intranasal immunization required B cells, as JHD mice (deficient in B cells) were not protected by intranasal immunization (FIG. 1E-FIG. 1G). In the absence of B cells, intranasal immunization was unable to control viral replication in the DRG and spinal cord (FIG. 1G).

Figure 5E:
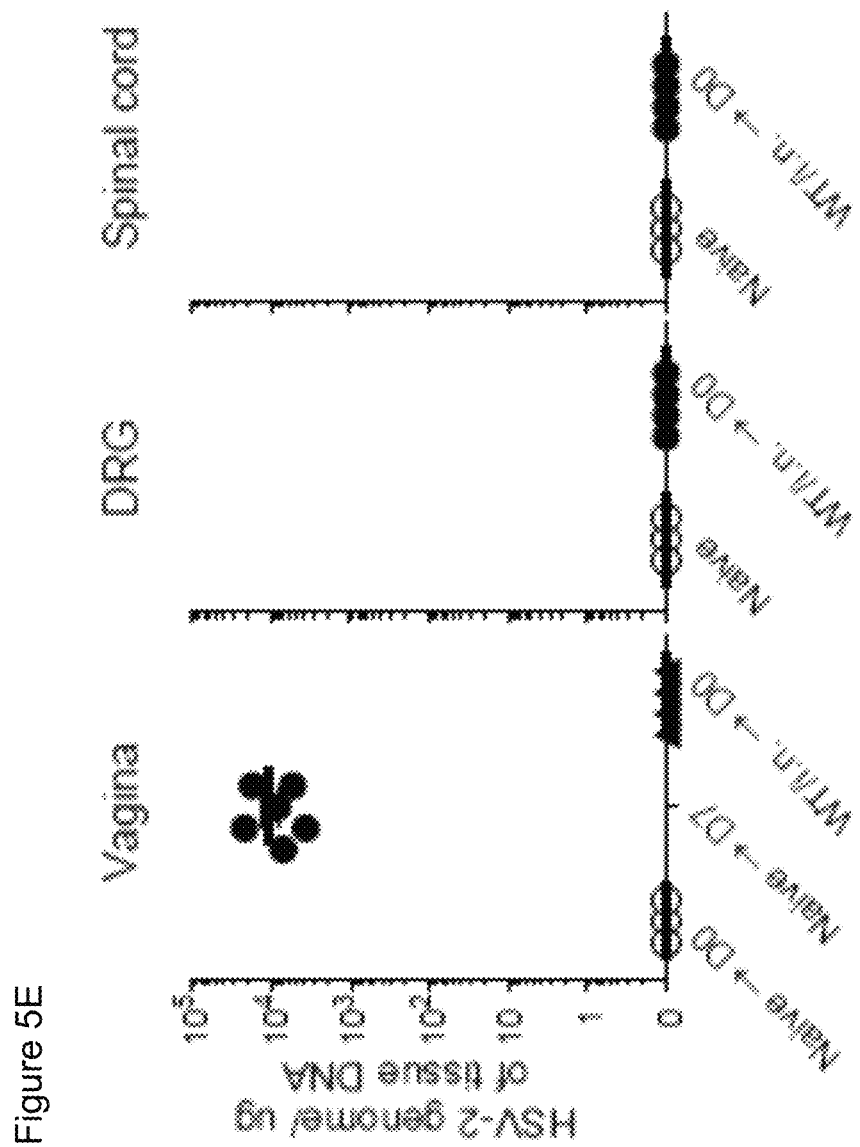

In mice immunized intranasally with TK⁻ HSV-2, no evidence of infection in the DRG or the spinal cord was found (FIG. 5E). Moreover, the intranasal route of immunization was not unique in conferring protective response, as parabiotic mice sharing circulation with intravaginally immunized partners were also partly protected from vaginal challenge with WT HSV-2 in the absence of $T_{RM}$ (Iijima, N. et al., 2014, Science 346, 93-98). (FIG. 5F-FIG. 5H). It was found that the B cells in the immunized partners were required to confer protection in the naive conjoined mice, as partners of immunized μMT mice were unprotected (FIG. 5F-FIG. 5H). Moreover, antigen-specific B cells were required to confer protection, as intravaginally immunized partners whose B cells bore an irrelevant B cell receptor (against hen egg lysozyme (HEL)) were unable to confer protection in the conjoined naive partner (FIG. 5F-FIG. 5H). As observed for the intranasal immunization, viral control conferred by the immunized parabiotic partner was not observed in the vaginal mucosa (FIG. 5H), demonstrating that protection occurs in the innervating neurons.

Figure 6A:
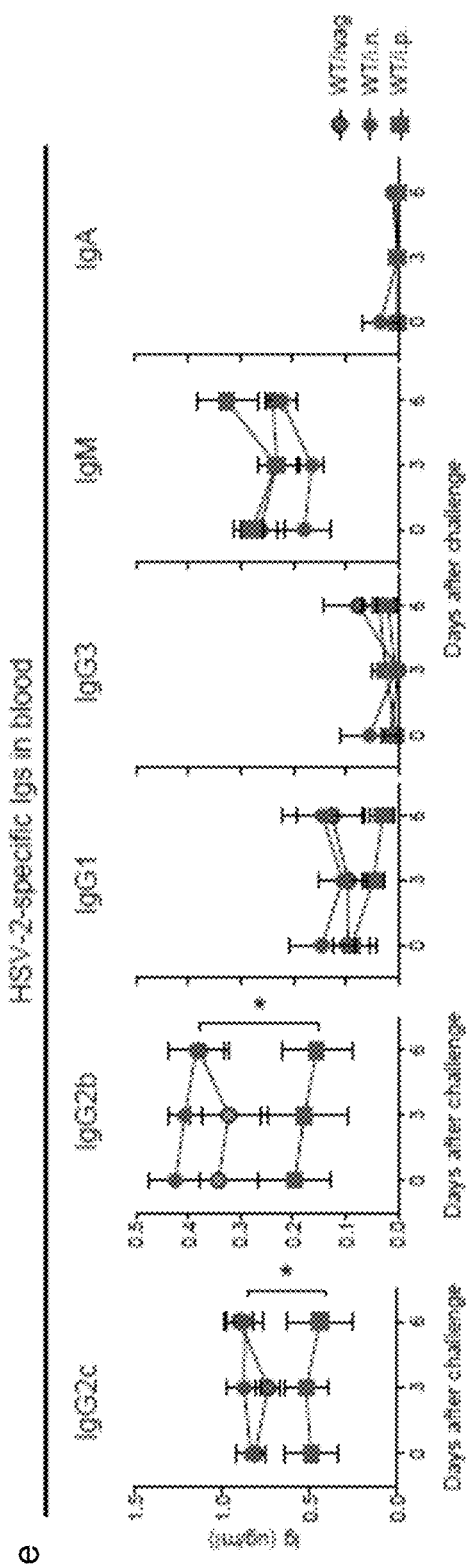
FIG. 6A and FIG. 6B are a set of images depicting the results of experiments demonstrating that mucosal TK− HSV-2 immunization generates higher levels of virus-specific IgG2b and IgG2c compared with intraperitoneal immunization. WT mice were immunized with TK− HSV-2 ($10^5$ p.f.u. per mouse) via intravaginal, intraperitoneal or intranasal routes. Six weeks later, these mice were challenged with a lethal dose of WT HSV-2 intravaginally. At the indicated days after challenge, HSV-2-specific Ig (FIG. 6A) and total Ig (FIG. 6B) in serum were analyzed by ELISA. Data are means±s.e.m. *P<0.05 (Mann-Whitney U-test).
Figure 6B:
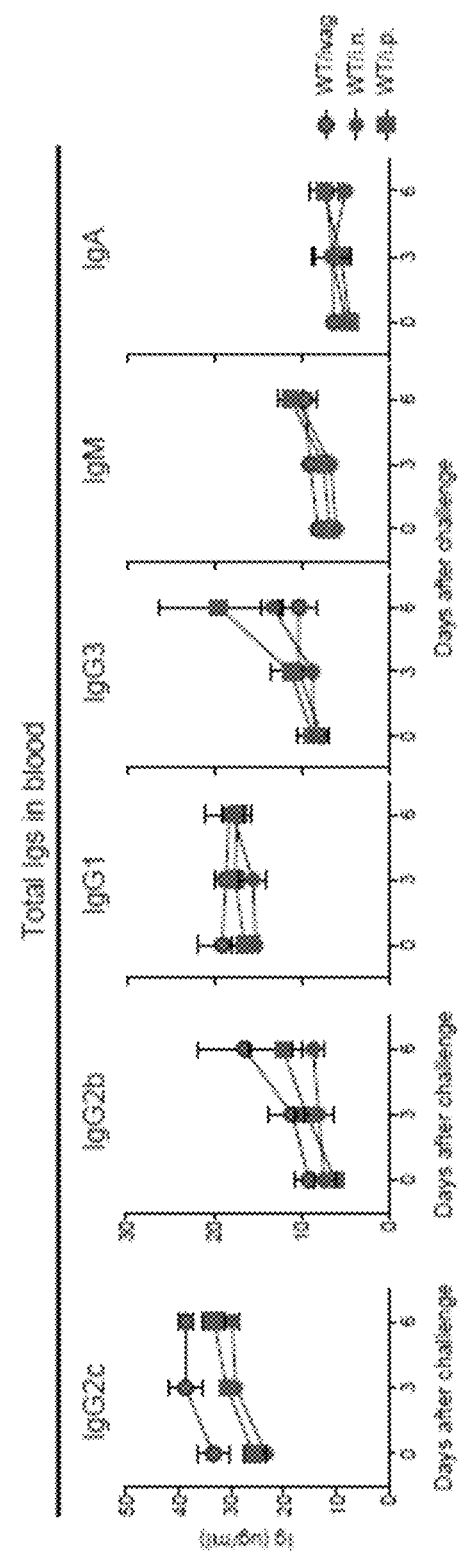

Next, the basis for superior protection by antibodies following different routes of immunization was investigated. Intravaginal, intranasal and intraperitoneal routes of immunization with TK⁻ HSV-2 results in comparable circulating CD4 T-cell memory responses (Iijima, N. et al., 2014, Science 346, 93-98). While no differences were seen for other isotypes, the intranasal and intravaginal routes of immunization were superior to intraperitoneal route in generating higher levels of systemic HSV-2-specific immunoglobulin-G (IgG)2b and IgG2c responses (FIG. 6A-FIG. 6B). These results indicated that higher levels of circulating virus-specific IgG2b and IgG2c correlate with protection against vaginal HSV-2 challenge.

Figure 2A:
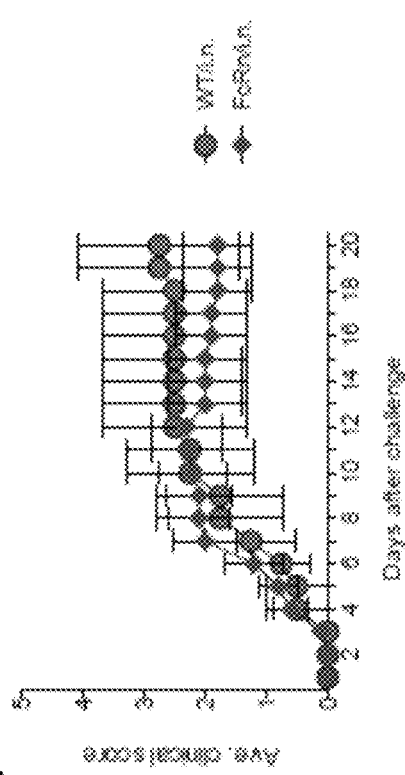
Figure 2B:
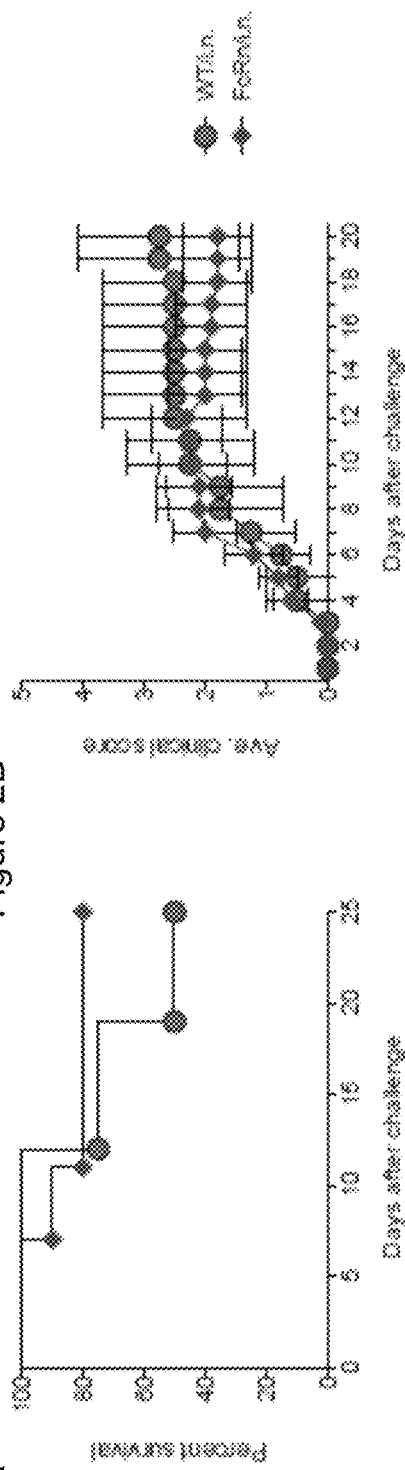

It was next determined how antibody access to the DRG and spinal cord is mediated. Even though the peripheral nervous tissues are protected from antibody diffusion through the blood-nerve barrier, it was formally possible that secretion of antibody into the tissue occurs through transport of serum antibody by the neonatal Fc receptor for IgG (FcRn)(Roopenian, D. C. et al.,2007, Nature Rev. Immunol. 7, 715-725) expressed on the endothelial cells within the infected tissues. However, it was found that mice deficient in FcRn immunized intranasally with TK− HSV-2 were equally protected as the WT counterpart from vaginal HSV-2 infection (FIG. 2A and FIG. 2B). Thus, circulating HSV-2-specific antibodies are somehow mobilized to the neuronal tissues following local viral infection in an FcRn-independent manner, and are required for protection of the host.

Figure 2C:
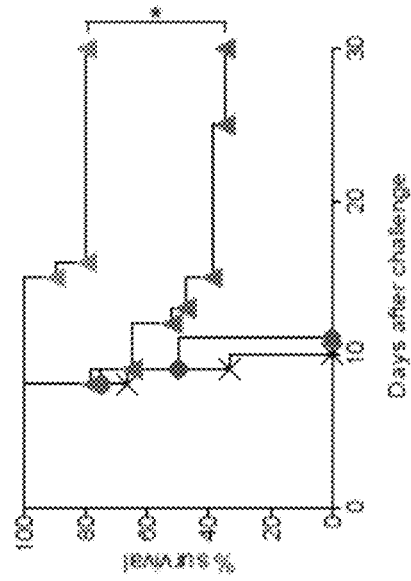
Figure 2D:
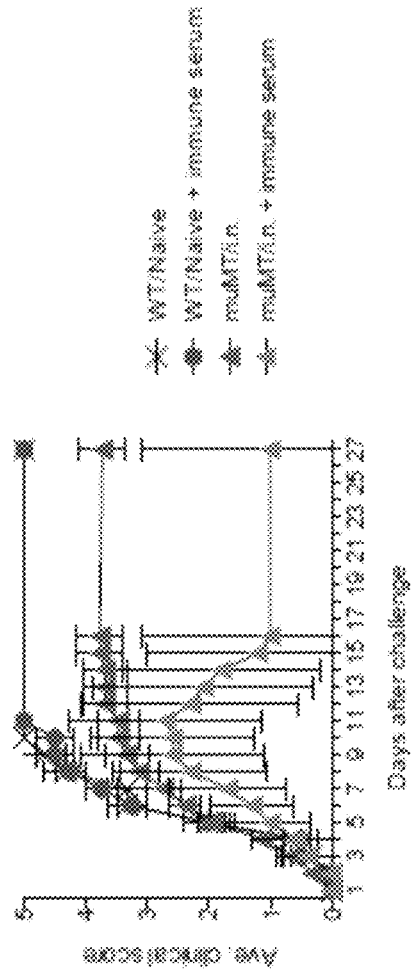

If circulating antibodies are sufficient, passive transfer of HSV-2-specific antibodies alone should be able to protect the host. However, it has been shown (McDermott, M. R. et al., 1990, J. Gen. Virol. 71, 1497-1504, Morrison, L. A. et al., 2001 J. Virol. 75, 1195-1204) that intravenous injection of HSV-2-specific antibodies alone fails to protect naive mice against HSV-2 challenge (FIG. 2C and FIG. 2D). In contrast, consistent with a previous study (Morrison, L. A. et al., 2001, J. Virol. 75, 1195-1204), it was discovered that B-cell-deficient µMT mice immunized intranasally with TK− HSV-2 and given systemic administration of HSV-2-specific antiserum were protected (FIG. 2C and FIG. 2D). Thus, these results demonstrate that it is the secreted antibodies, and not B cells themselves, in concert with non-B-cell immune cells, probably T cells induced by immunization, that seem to be required for protection. To test this possibility, CD4 T cells from mice previously immunized were depleted intranasally just before intravaginal HSV-2 challenge. In this setting, differentiation of B cells and antibody responses were allowed to occur fully in the presence of CD4 T-cell help for 6 weeks. Mice acutely depleted of CD4 T cells succumbed to infection with HSV-2 (FIG. 2E and FIG. 2F), whereas depletion of CD8 T cells and natural killer (NK) cells had no effect (Sato, A. et al., 2014, J. Virol. 88, 13699-13708). Moreover, neutralization of IFN-γ before challenge, or genetic deficiency in IFN-γR, also rendered intranasally immunized mice more susceptible to intravaginal HSV-2 challenge (FIG. 2E and FIG. 2F). Of note, depletion of CD4 T cells from intranasally immunized mice just before the viral challenge rendered mice incapable of viral control in the DRG, to a similar extent as the immunized B-cell-deficient µMT mice (FIG. 2G). It was observed that intranasal immunization conferred near-complete protection from HSV-2 in the DRG but variable protection in the spinal cord (FIG. 1D and FIG. 2G). Because HSV-2 can differentially seed the DRG and spinal cord through sensory neurons and autonomic neurons (Ohashi, M. et al., 2011, J. Virol. 85, 3030-3032), these data demonstrate that the efficacy of antibody-mediated protection may depend on the route of viral entry. Further, these results indicate that circulating antibodies, CD4 T cells and IFN-γ collectively mediate neuroprotection against HSV-2.

Figure 7A:
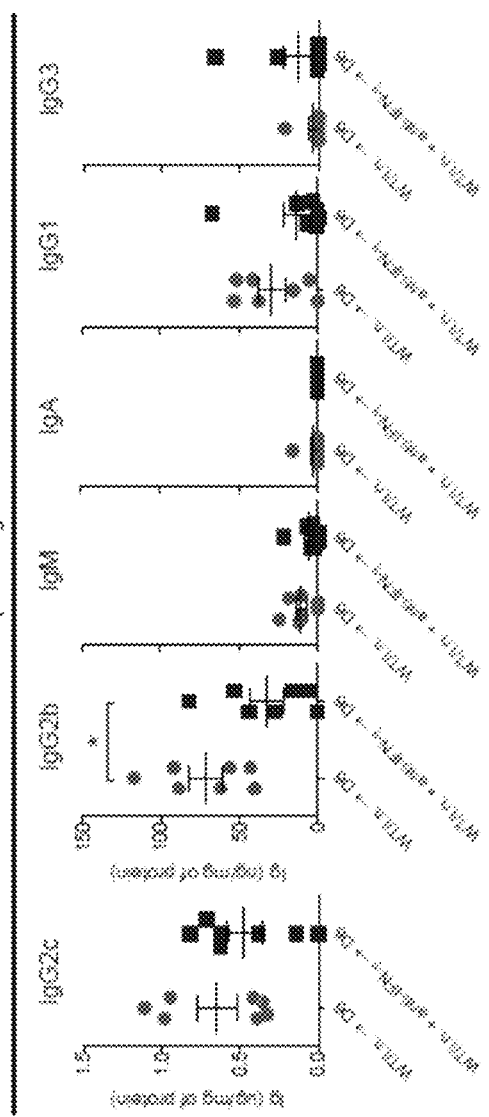
FIG. 7A and FIG. 7B are a set of images depicting the results of experiments demonstrating that the enhancement of antibody access to the DRG with IFN-γ. WT mice immunized with TK– HSV-2 ($10^5$ p.f.u. per mouse) intranasally 6 weeks earlier were challenged with a lethal dose of WT HSV-2 intravaginally. Six days after challenge, after extensive perfusion, HSV-2-specific (FIG. 7A) and total Ig (FIG. 7B) in DRG homogenates were analyzed by ELISA. Depletion of CD4 T cells or neutralization of IFN-γ was performed on days –4, and –1, 2 and 4 days after challenge by intravenous injection of anti-CD4 (GK1.5) or anti-IFN-γ (XMG1.2), respectively. Data are means±s.e.m. *P<0.05; **P<0.001 (two-tailed unpaired Student's t-test).
Figure 7B:
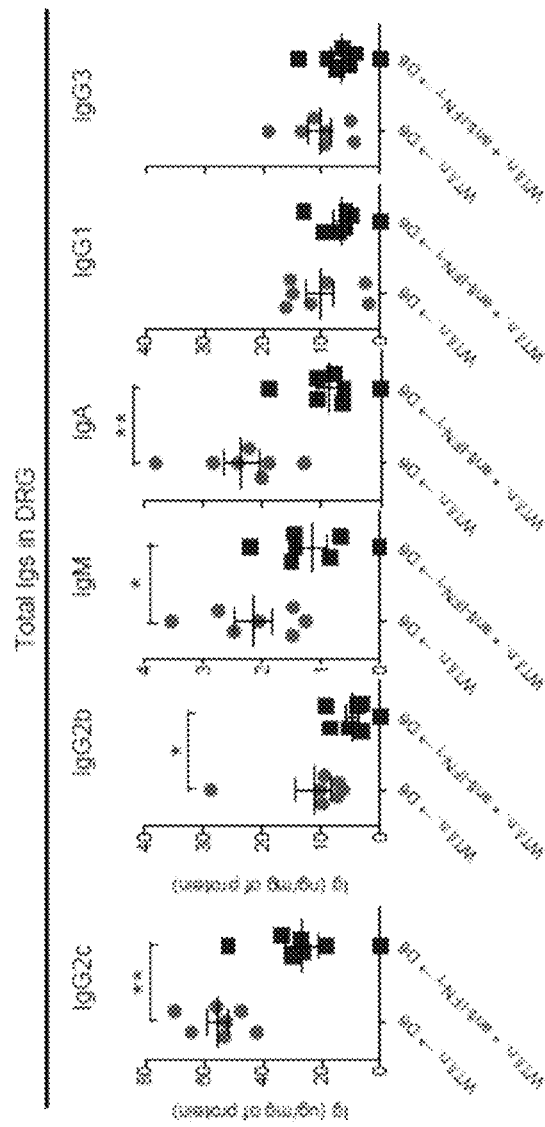
Figure 8A:
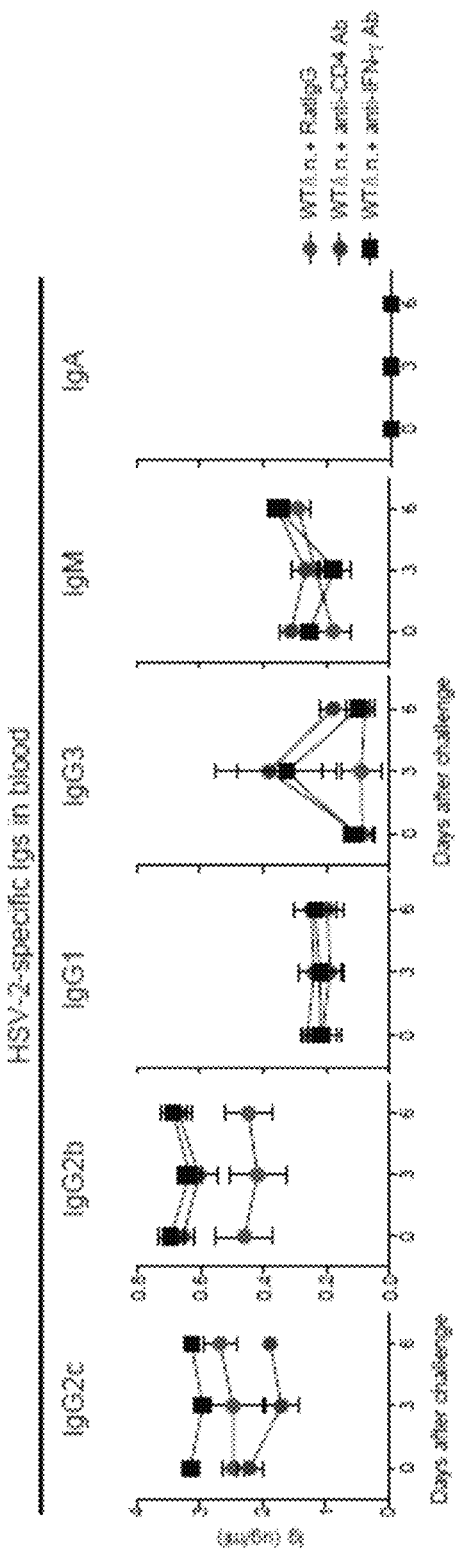
FIG. 8A through FIG. 8D, are a set of images depicting the results of experiments investigating the neutralization of IFN-γ, demonstrating that α4-integrin or depletion of CD4 T cells has no impact on circulating immunoglobulin levels.
Figure 8B:
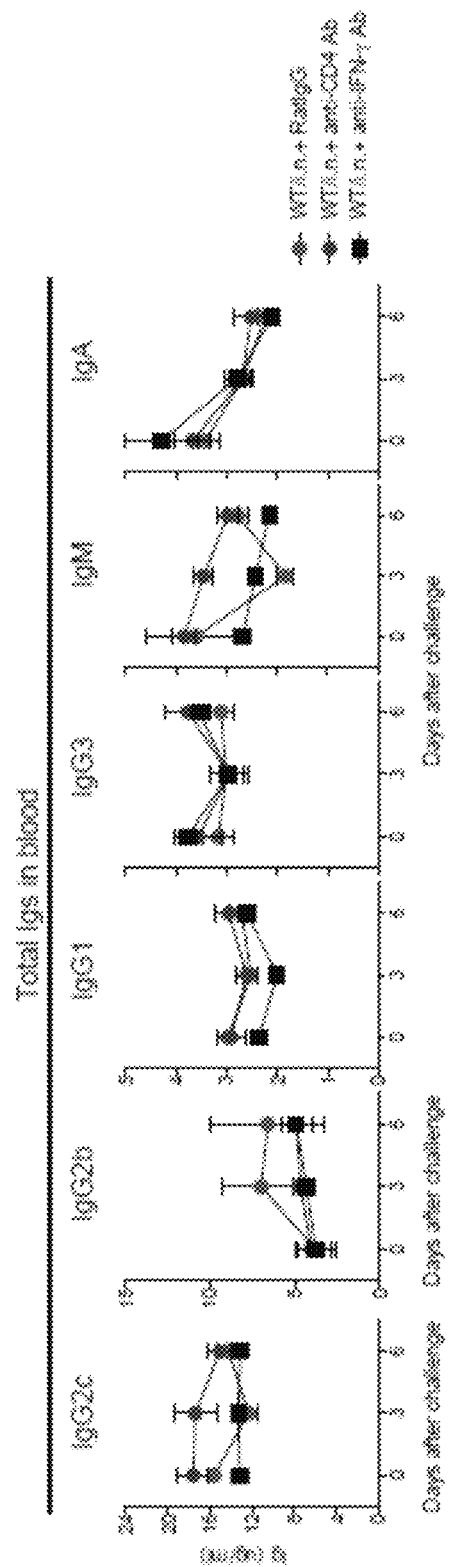

Given that antibody-mediated protection occurs at the level of the innervating neurons and not within the vagina (FIG. 1C and FIG. 5H), it is hypothesized that CD4 T cells will control delivery of antibodies to the tissue parenchyma through secretion of IFN-γ. Low levels of virus-specific and total antibodies were detected in the DRG or spinal cord at steady state in immunized mice (FIG. 3A-FIG. 3D; WT/intranasally→D0), and undetectable levels of antibodies in these tissues in previously unimmunized mice 6 days after an acute infection with HSV-2 (FIG. 3A-FIG. 3D; WT/naive→D6). However, in mice immunized intranasally with TK− HSV-2 6 weeks earlier, increase in the levels of antibodies was detected 6 days after intravaginal HSV-2 challenge within the DRG and in the spinal cord (FIG. 3A-FIG. 3D; WT/intranasally→D6). Moreover, CD4 T cells were required for access of virus-specific antibodies to the restricted tissue such as the DRG, as depletion of CD4 T cells completely diminished antibody levels in this tissue and spinal cord (FIG. 3D; WT/intranasally+anti-CD4→D6). Further, similar requirement for CD4 T cells (FIG. 3B, FIG. 3D) and IFN-γ (FIG. 7A-FIG. 7B) was found for diffusion of total IgG2b and IgG2c isotypes into the DRG, demonstrating that the delivery mechanism does not discriminate virus-specificity of the antibodies. In contrast to the neuronal tissues, acute depletion of CD4 or IFN-γ blockade once antibody responses were established had no significant impact on the serum levels of anti-HSV-2 or total antibodies (FIG. 8A and FIG. 8B). To determine whether antigen-specific memory CD4 T cells were required to mediate antibody access to the neuronal tissues, mice were primed intranasally with a heterologous virus, influenza A virus and, 4 weeks later, were challenged with HSV-2 intravaginally. In contrast to mice harboring cognate memory CD4 T cells, antibody access to neuronal tissues following intravaginal HSV-2 challenge was not observed in mice that had irrelevant memory CD4 T cells (against influenza A virus) (FIG. 9A-FIG. 9D). These data indicate that antigen-specific memory CD4 T cells are required for antibody access to the neuronal tissues.

Figure 4A:
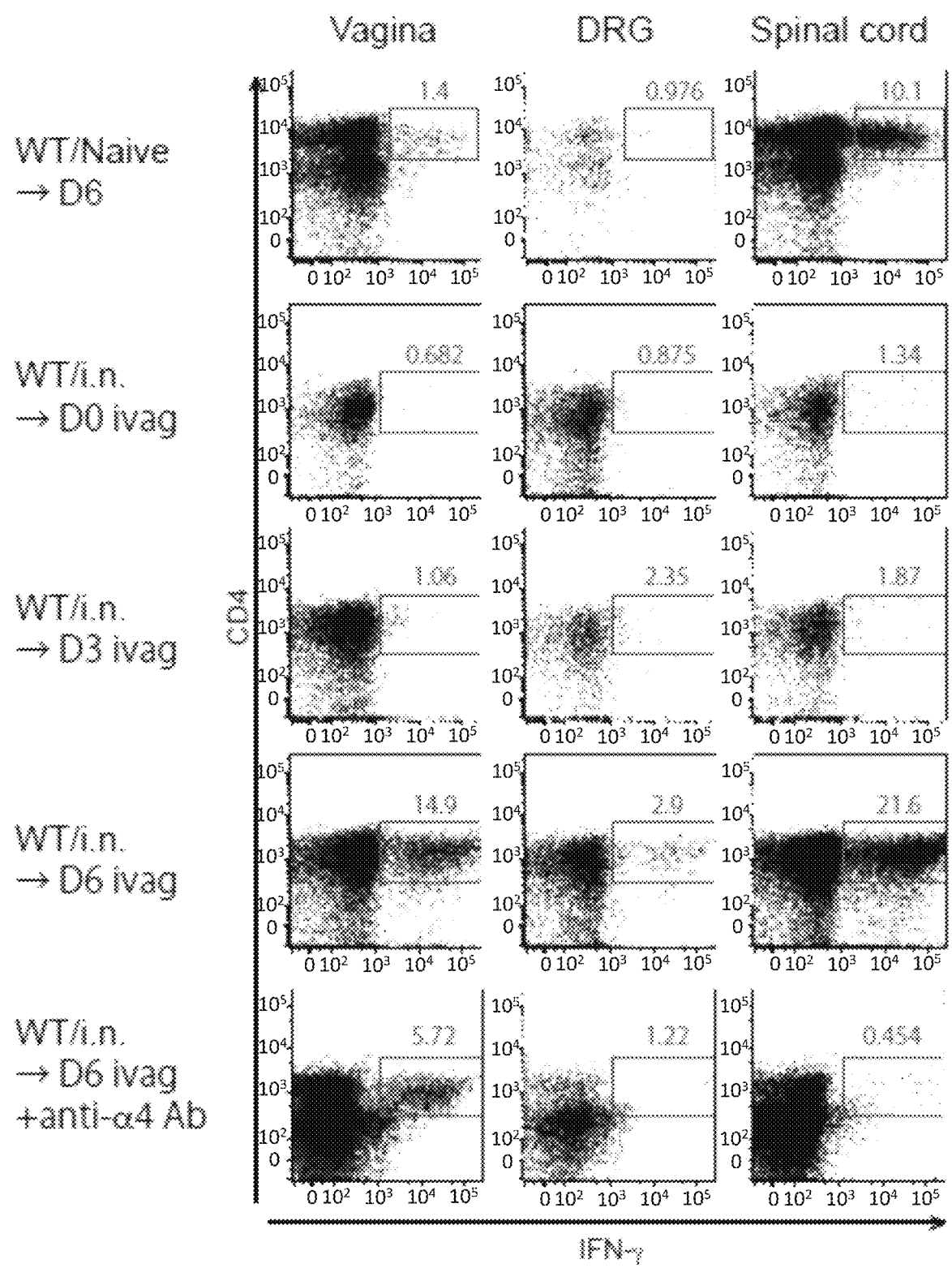
FIG. 4A through FIG. 4F are a set of images depicting the results of experiments demonstrating that α4-Integrin-dependent recruitment of memory CD4$^+$T cells required for antibody access to neuronal tissues. WT mice immunized intranasally with TK−HSV-2 6 weeks earlier were challenged with a lethal dose of WT HSV-2. Neutralization of α4-integrin was performed on days 2 and 4 after challenge by intravenous injection of anti-α4 integrin (CD49d) antibody.
Figure 10A:
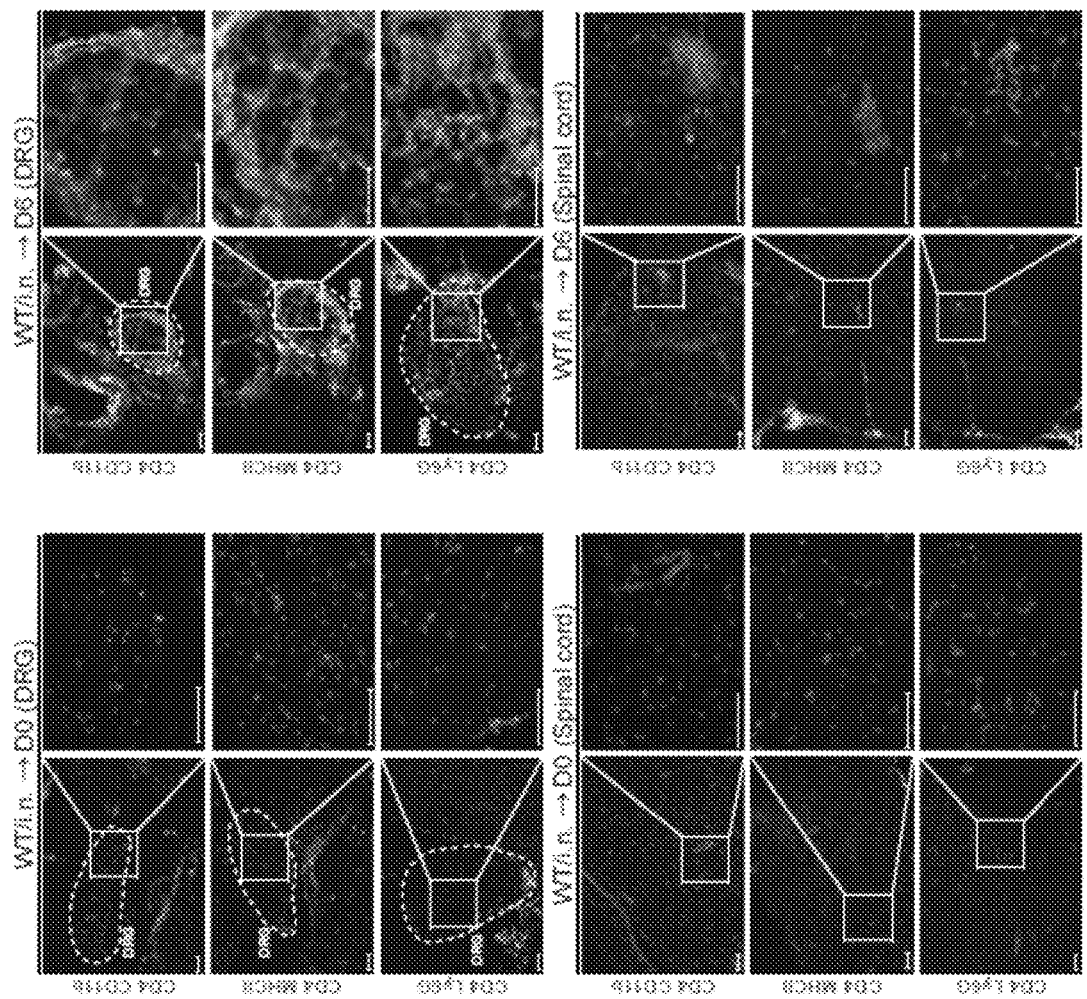
FIG. 10A and FIG. 10B are a set of images depicting the results of experiments demonstrating that most CD4 T cells recruited to the DRG and spinal cord of immunized mice are localized in the parenchyma of neuronal tissues.

It was hypothesized that memory CD4 T cell might enter the barrier-protected tissues and mobilize antibody access through local secretion of IFN-γ. In support of this idea, it was found that IFN-γ-secreting HSV-2-specific CD4 T cells entered the DRG and spinal cord around 6 days after genital HSV-2 challenge in mice that received intranasal immunization 6 weeks previously (FIG. 4A and FIG. 4B; WT/intranasally→D6). Some increase in innate leukocytes bearing CD11b, Ly6G or MHCII was observed in DRG and spinal cord 6 days after challenge (FIG. 10A). IFN-γ secretion was confined to the memory CD4 T-cell population within the DRG (FIG. 4A). Moreover, entry of effector CD4 T cells to the DRG and spinal cord at 6 days after primary vaginal HSV-2 infection was much less efficient than their memory counterpart (FIG. 4A and FIG. 4B; WT/naive→D6), demonstrated the intrinsic ability of T cells to migrate into these neuronal tissues is enhanced with memory development.

Figure 4B:
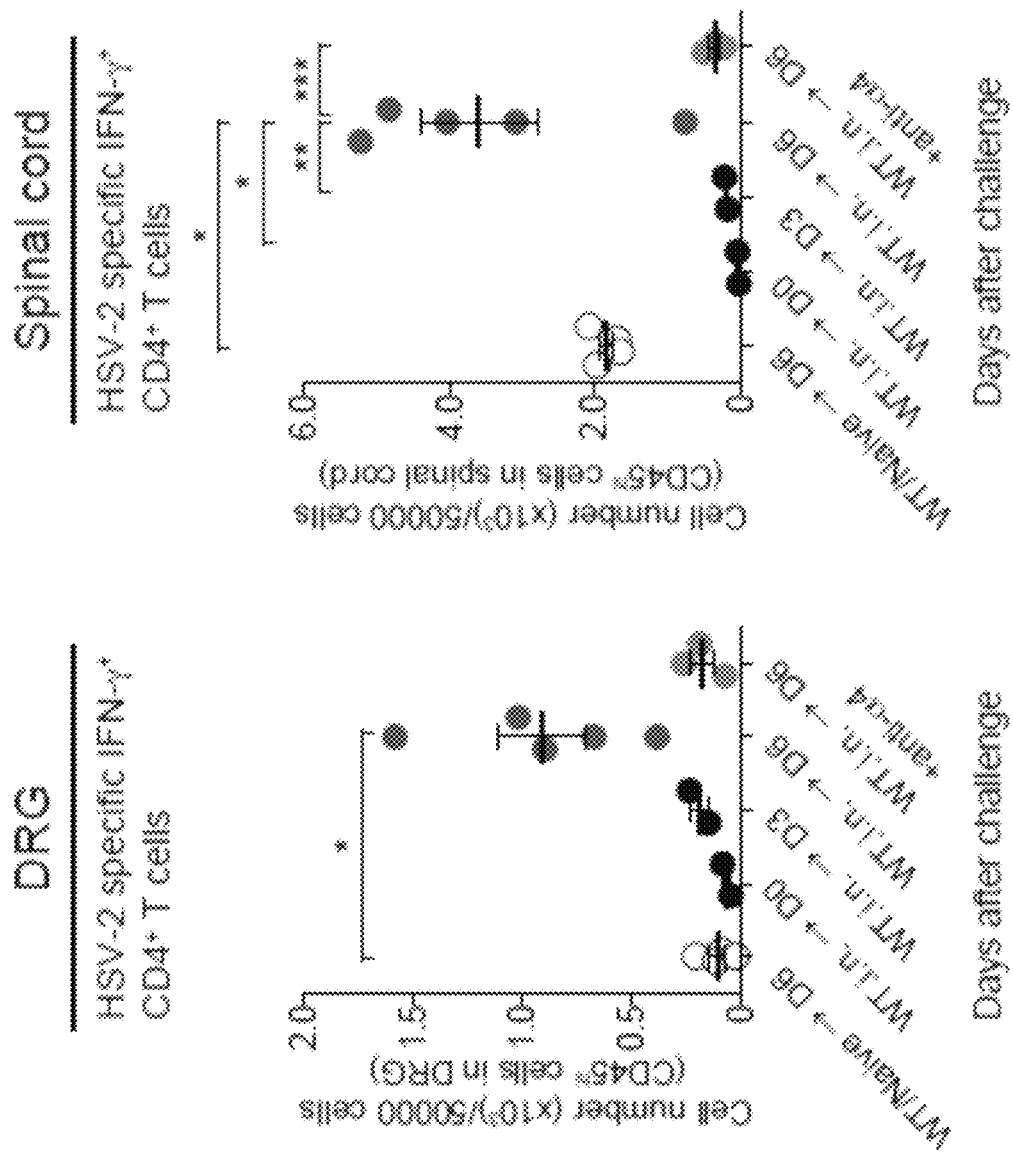
Figure 4D:
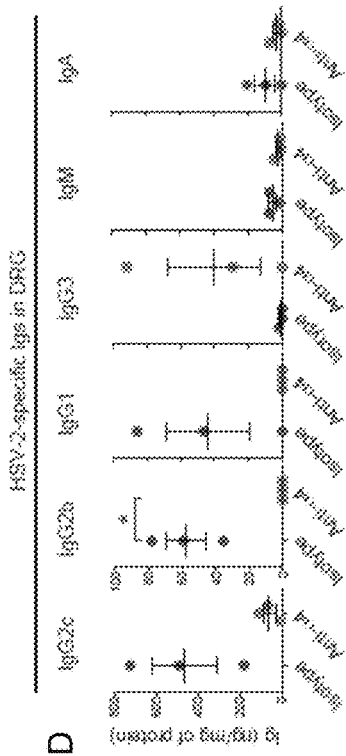
Figure 4E:
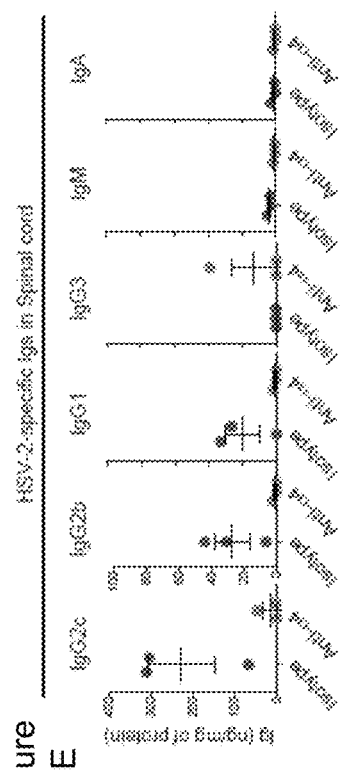
Figure 4F:
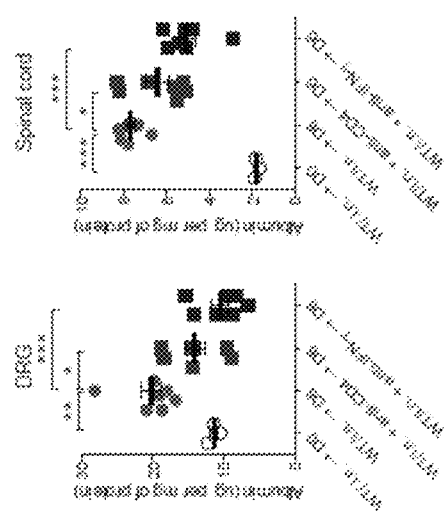
Figure 4C:
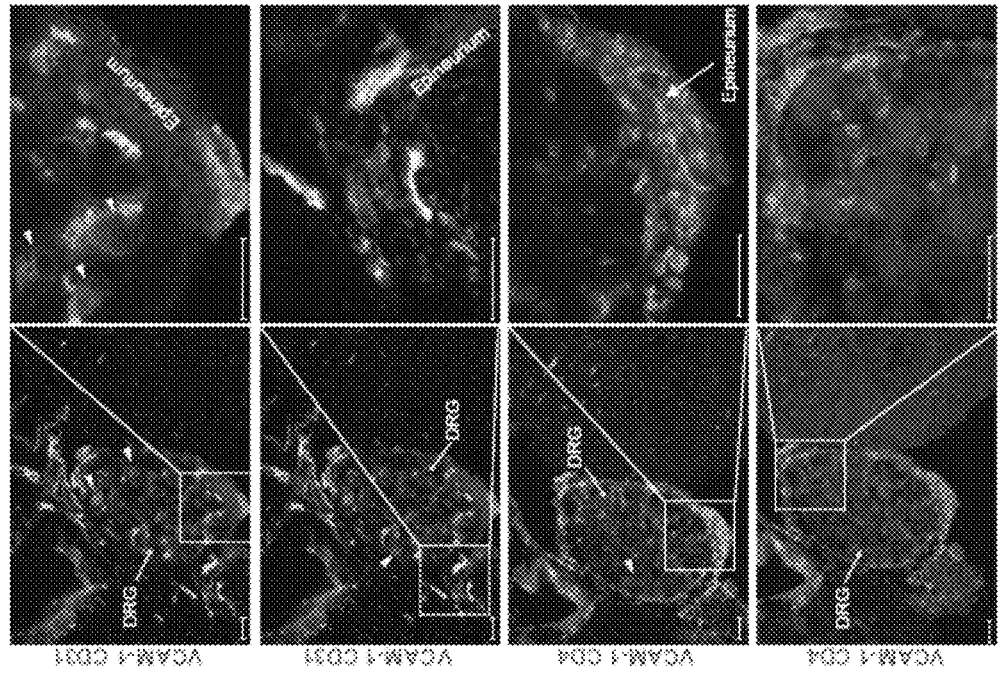
Figures 8C, 8D:
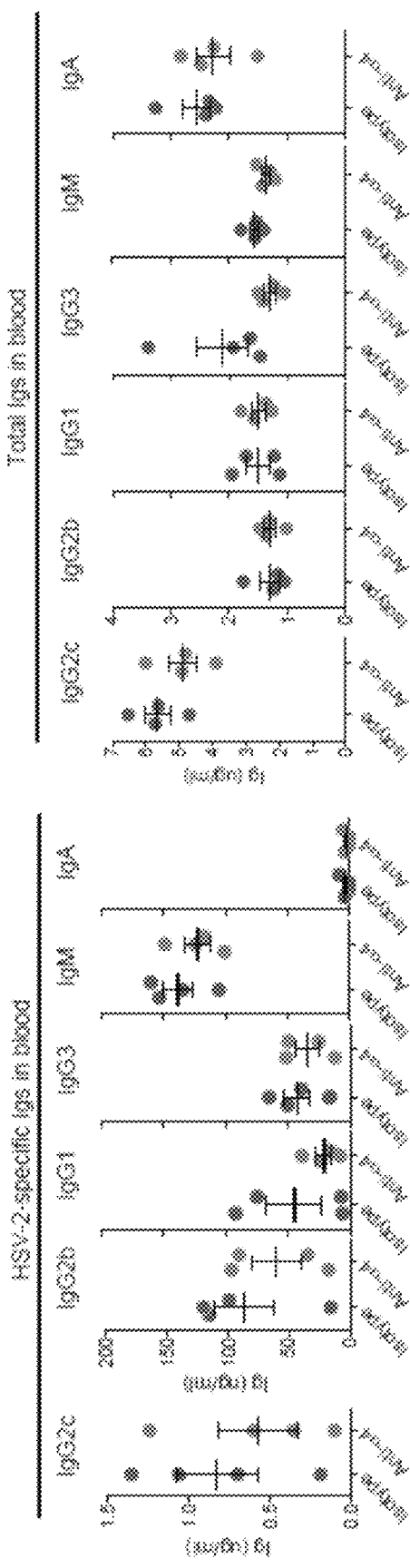
Figure 9A:
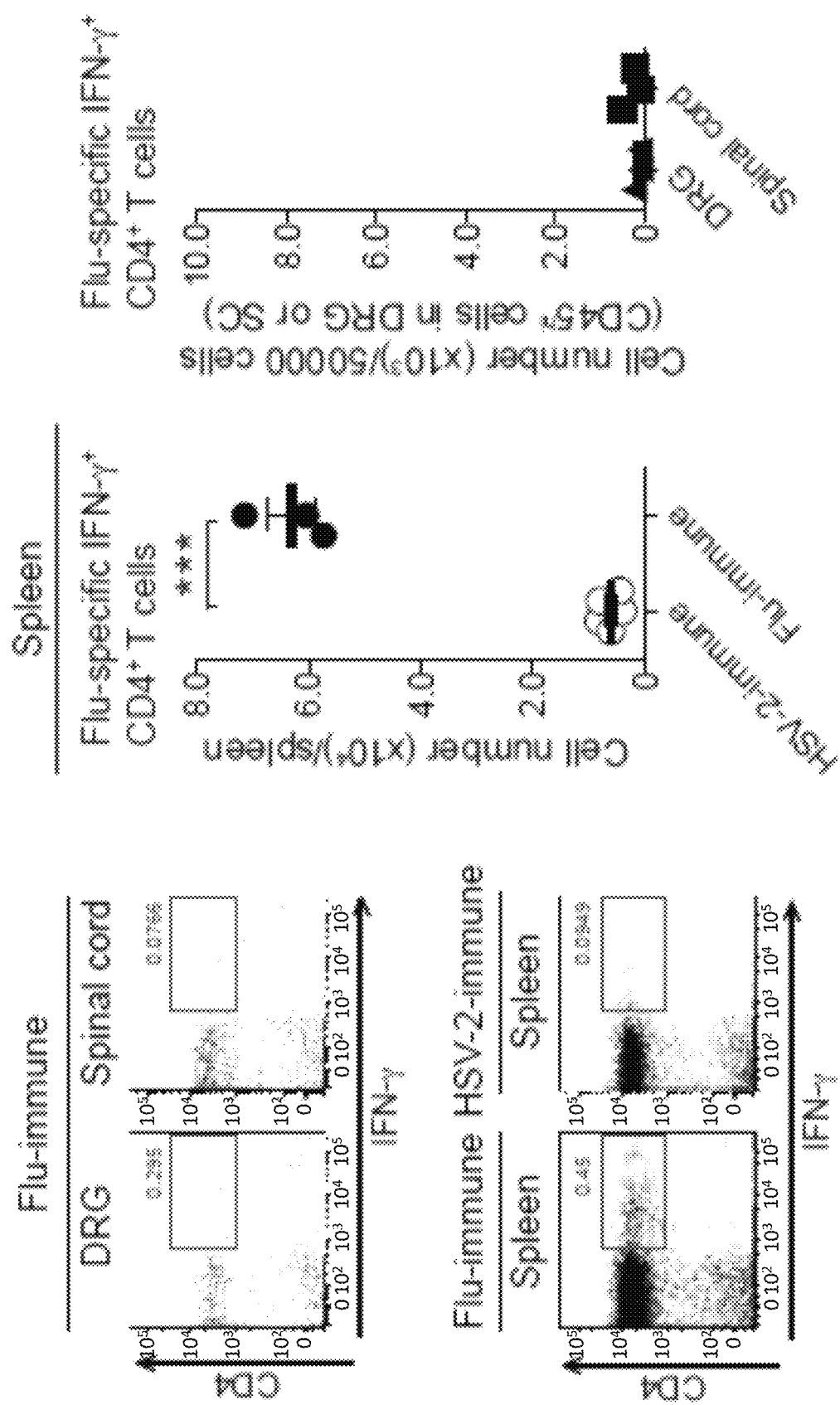
FIG. 9A through FIG. 9D are a set of images depicting the results of experiments demonstrating that an irrelevant immunization failed to increase the levels of total antibodies in neuronal tissues.
Figure 9B:
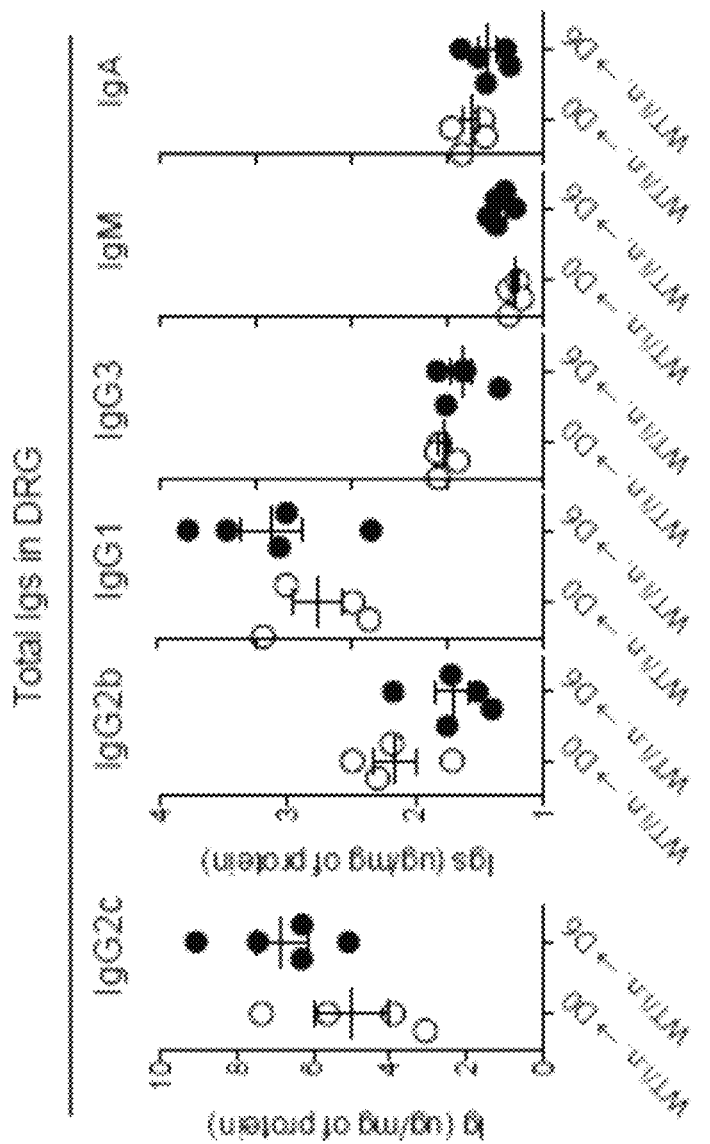
Figure 9C:
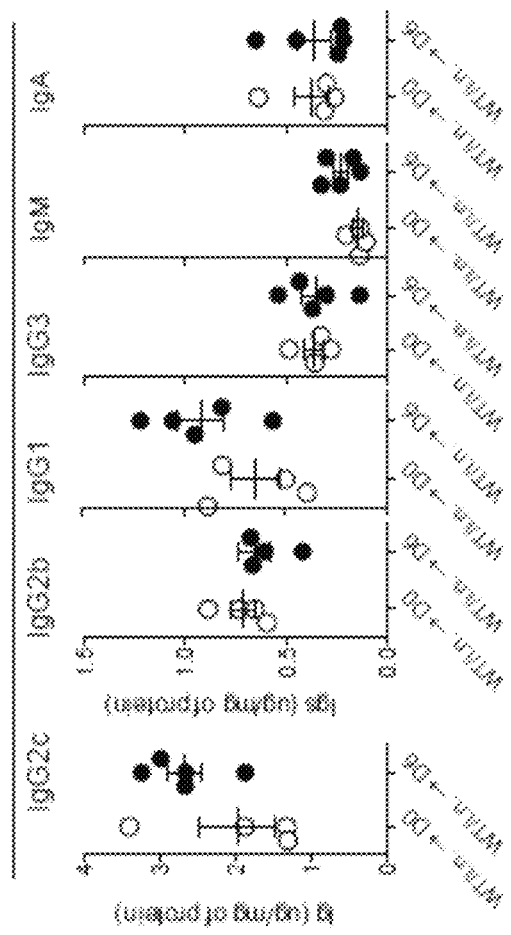
Figure 9D:
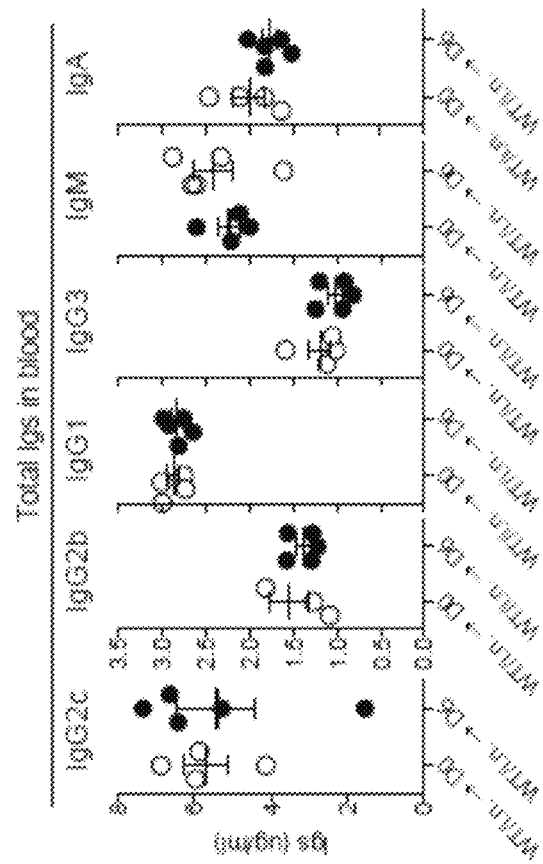
Figure 10B:
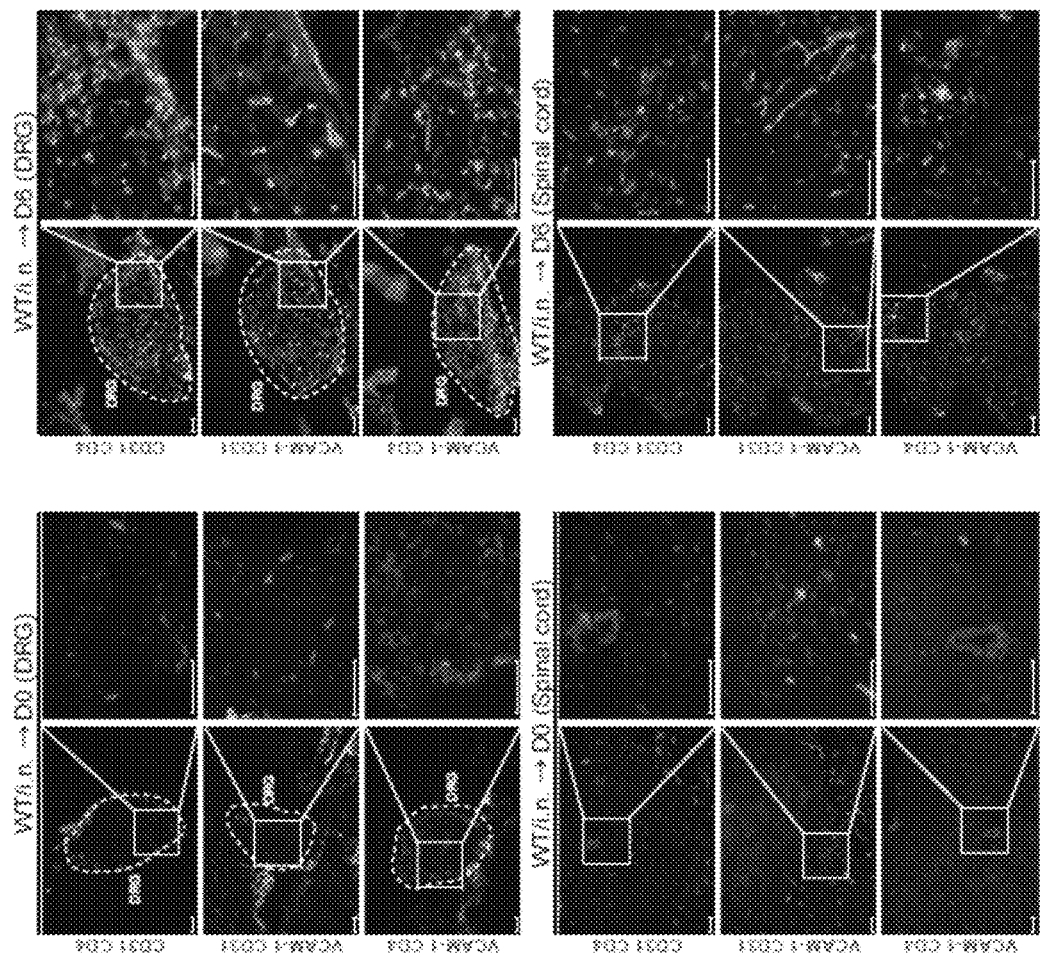
Figure 11A:
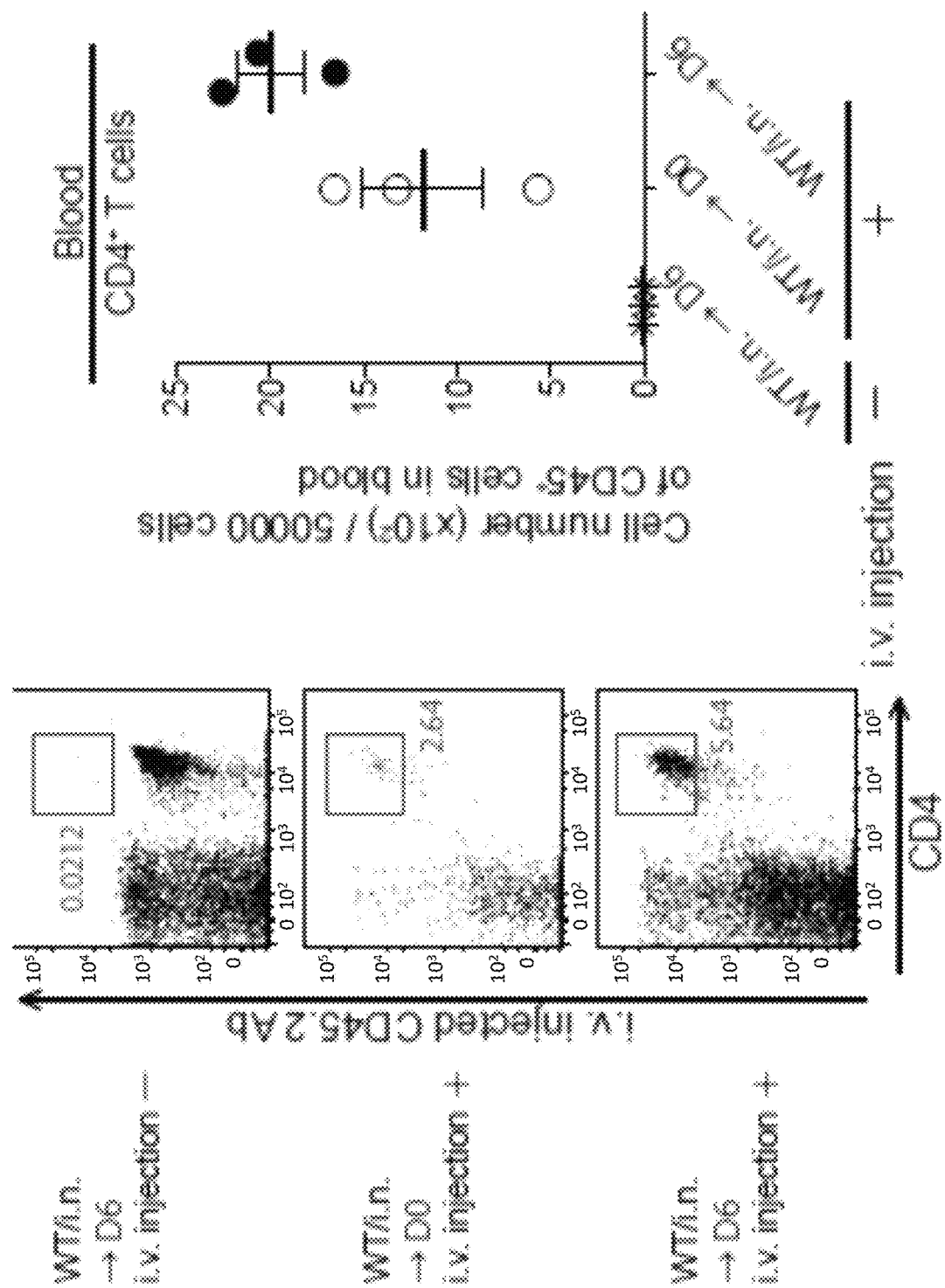
FIG. 11A and FIG. 11B are a set of images depicting the results of experiments demonstrating that intravascular staining reveals the localization of CD4 T cells in the parenchyma of neuronal tissues.
Figure 11B:
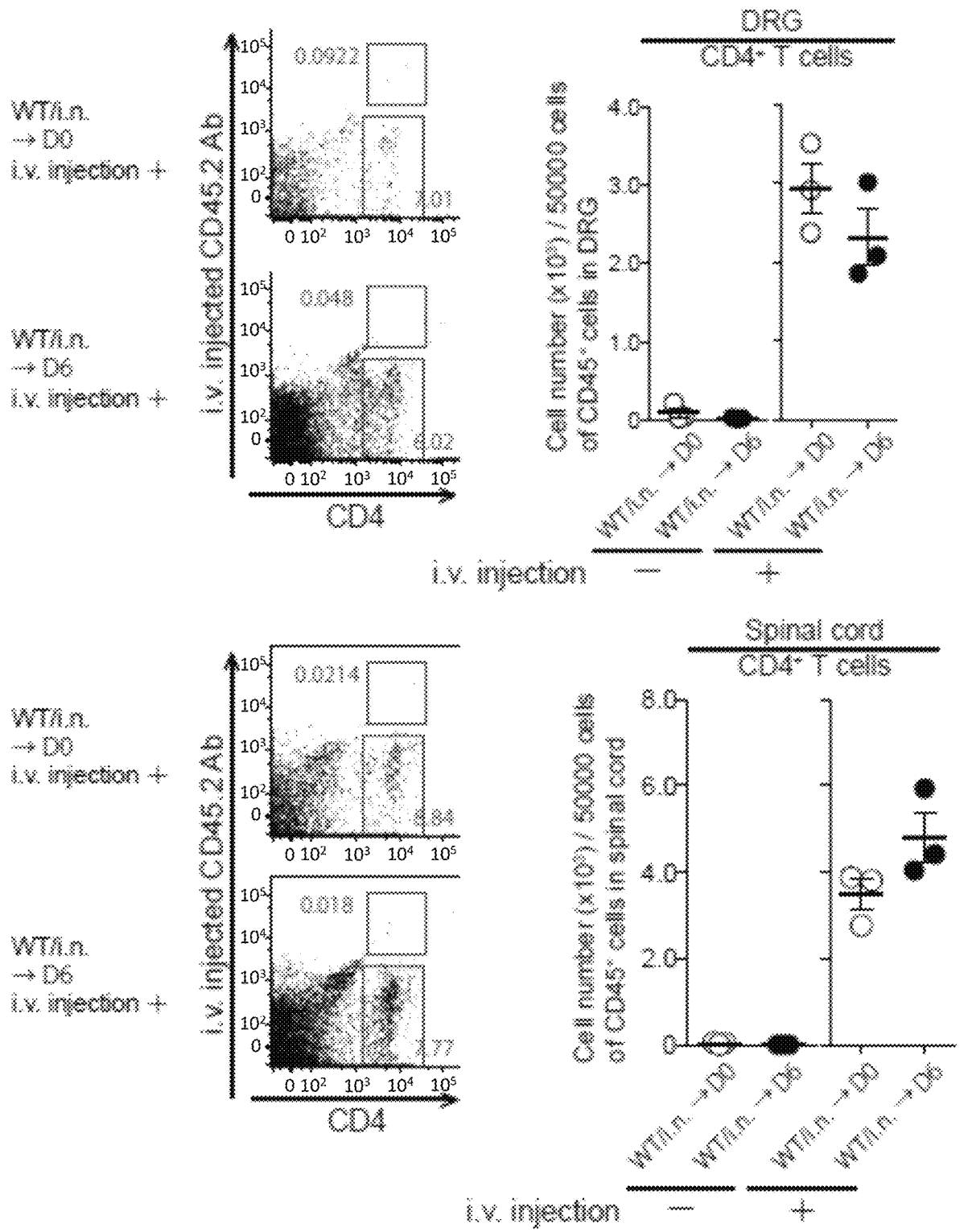

Interaction of α4β1 (or VLA4) and VCAM-1 contributes to T-cell recruitment across the blood-brain barrier (Man, S. et al., 2007, Brain Pathol. 17, 243-250). Memory CD4 T cells generated against HSV-2 expresses CD49d which is the integrin α4 subunit (Iijima, N. et al., 2014, Science 346, 93-98). It was found that the entry of memory CD4 T cells into the nervous tissue was strictly dependent on α4 integrin, as antibody blockade of α4 prevented their entry into the DRG and spinal cord (FIG. 4A and FIG. 4B). The expression of ligand for α4β1, VCAM-1, was observed in the endothelium of DRG and spinal cord in immune-challenged mice (FIG. 4C and FIG. 10B). Further, analysis of tissue sections revealed that the CD4 T cells were found in the parenchyma of the DRG and spinal cord, as well as within their epineurium and meninges, but not within the vasculature (FIG. 4C, FIG. 10A and FIG. 10B). Notably, many CD4 T cells were found adjacent to the cell body of neurons within the DRG. Some VCAM-1 staining was found in the cytosol of neuronal cell bodies (arrowhead FIG. 4C). Additionally, intravascular staining (Anderson, K. G. et al., 2014. Nature Protocols 9, 209-222) with antibody to CD90.2 revealed that the vast majority of the CD4 T cells in the DRG and spinal cord are sequestered from circulation (FIG. 11A, FIG. 11B). Thus, CD4 T cells recruited to the neuronal tissues access the parenchyma of the DRG and spinal cord. Notably, α4 integrin blockade of CD4 T-cell recruitment resulted in diminished access of virus-specific antibody to the DRG and spinal cord (FIG. 4D and FIG. 4E), with no effect on blood levels of virus-specific antibody (FIG. 8C) or the total antibody levels of various isotypes in circulation (FIG. 8D). Collectively, these data indicate that memory CD4 T cells enter the neuronal tissue and secrete IFN-γ to promote antibody access to the DRG and spinal cord.

Figure 12A:
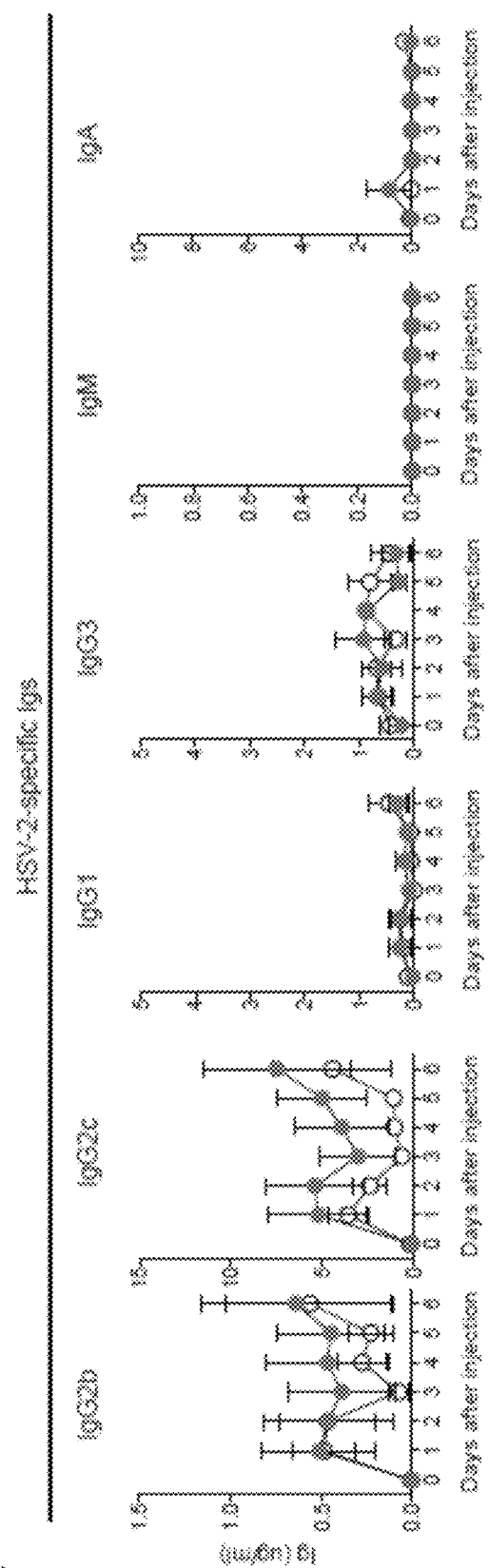
FIG. 12A through FIG. 12C are a set of images depicting the results of experiments demonstrating increased epithelial and vascular permeability in vaginal tissues using recombinant IFN-γ.
Figure 12B:
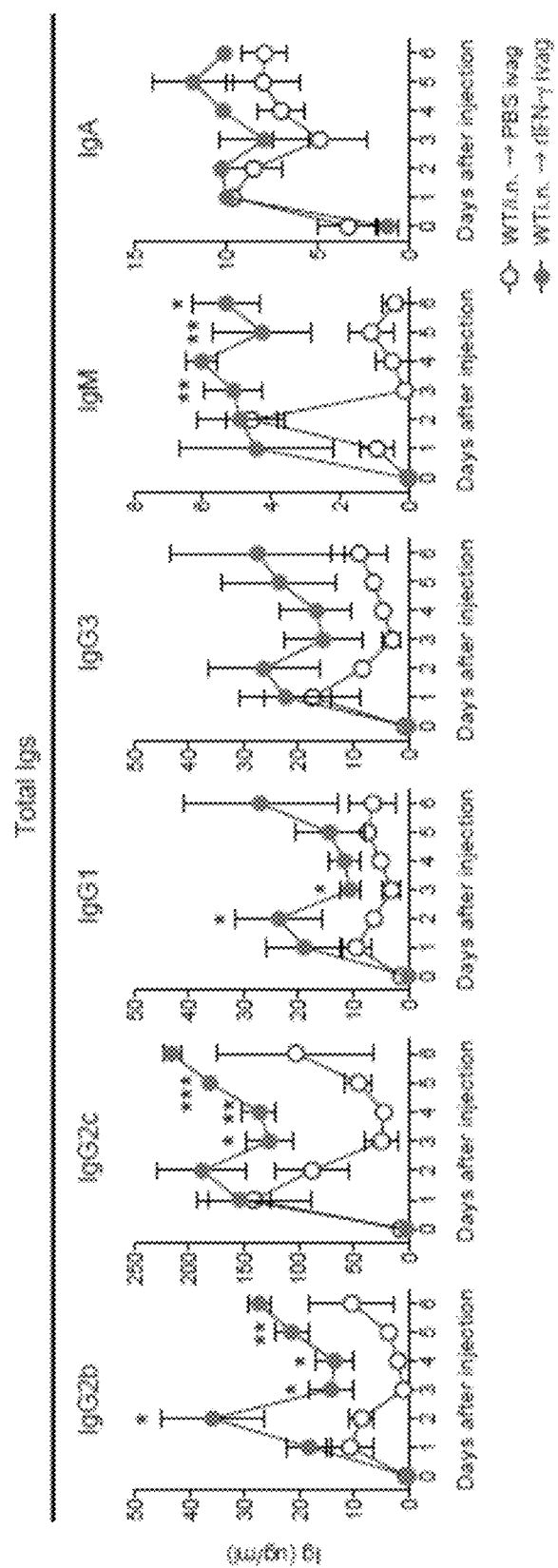
Figure 12C:
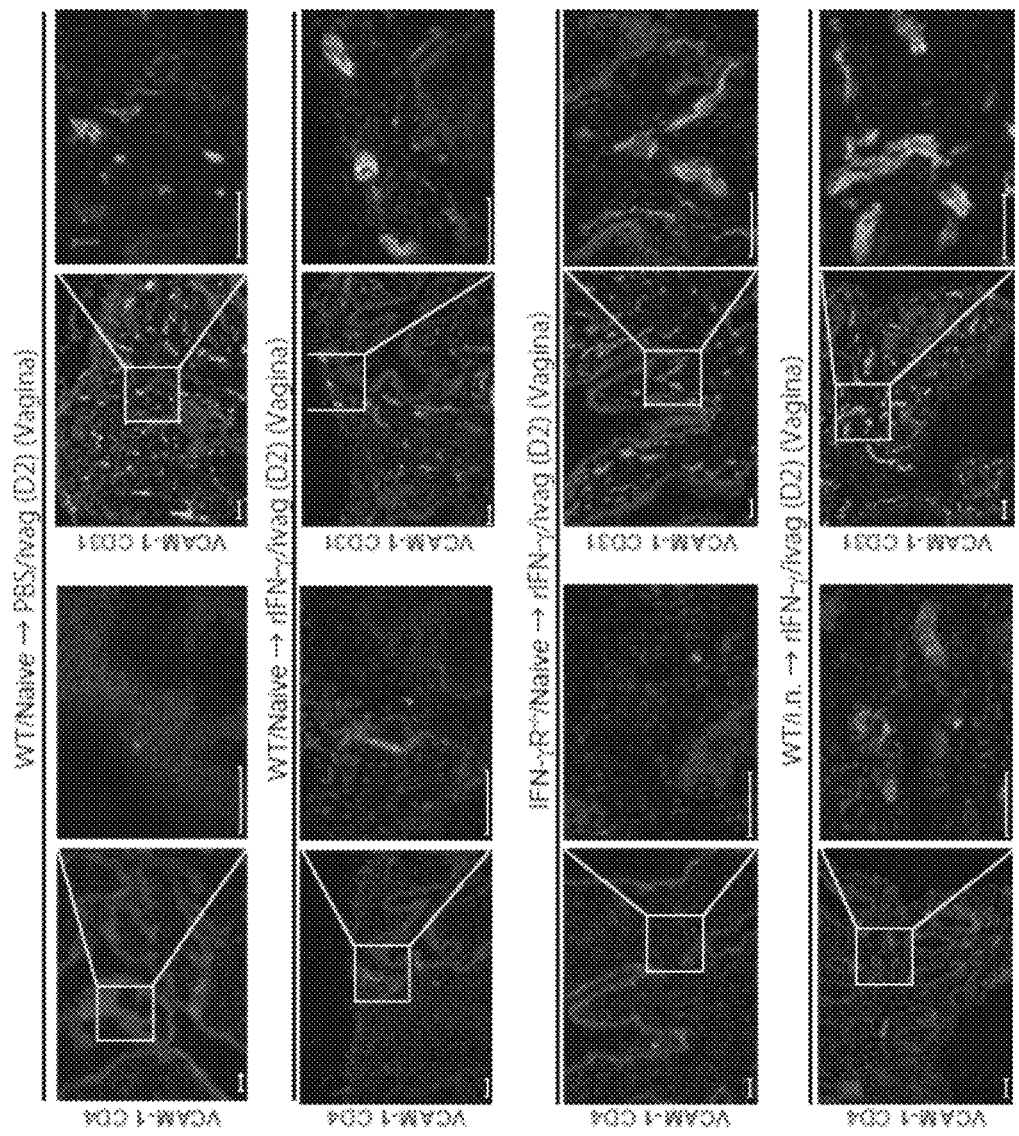
Figure 13A:
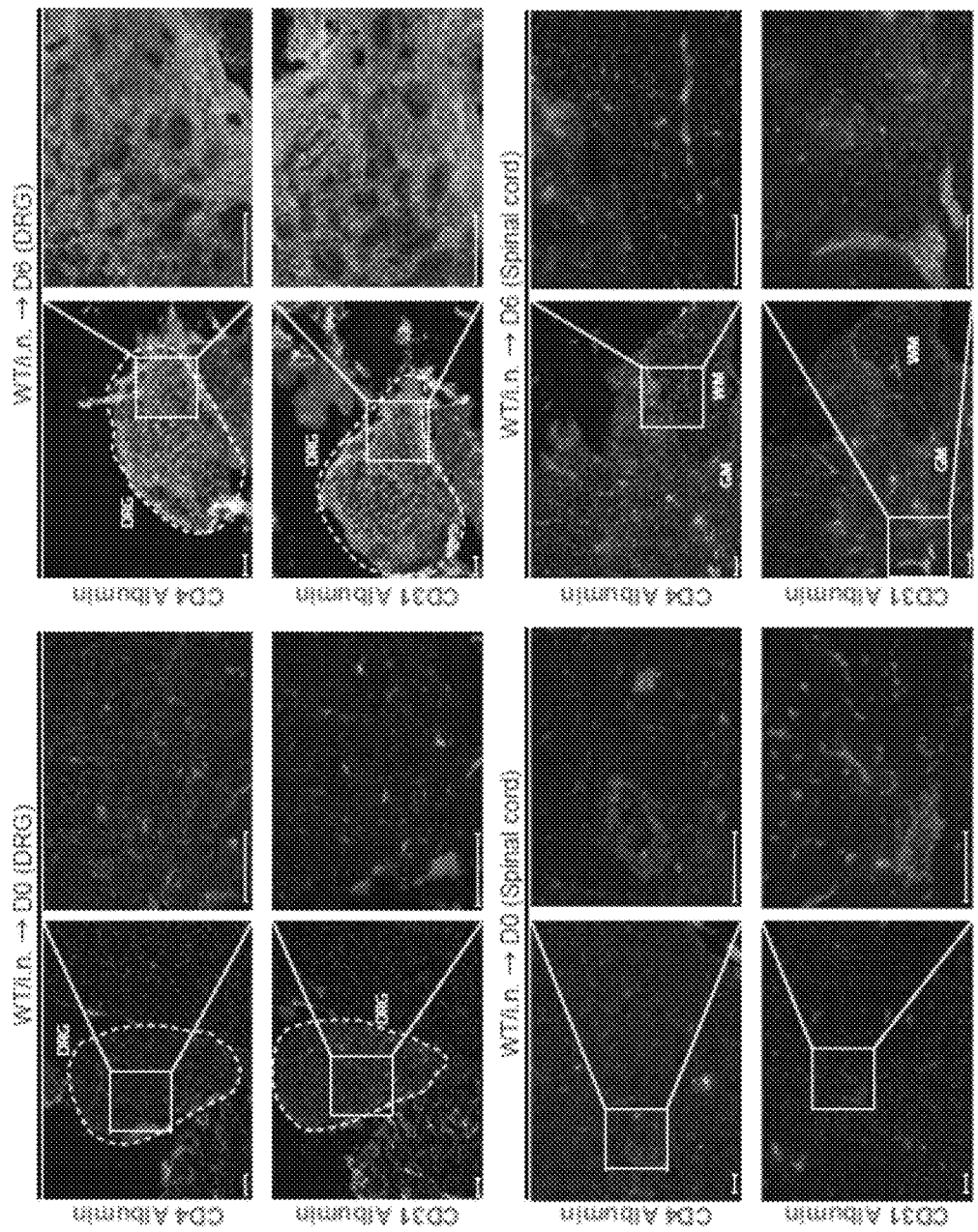
FIG. 13A and FIG. 13B are a set of images depicting the results of experiments demonstrating vascular permeability in DRG and spinal cord augmented following WT HSV-2 challenge.
Figure 13B:
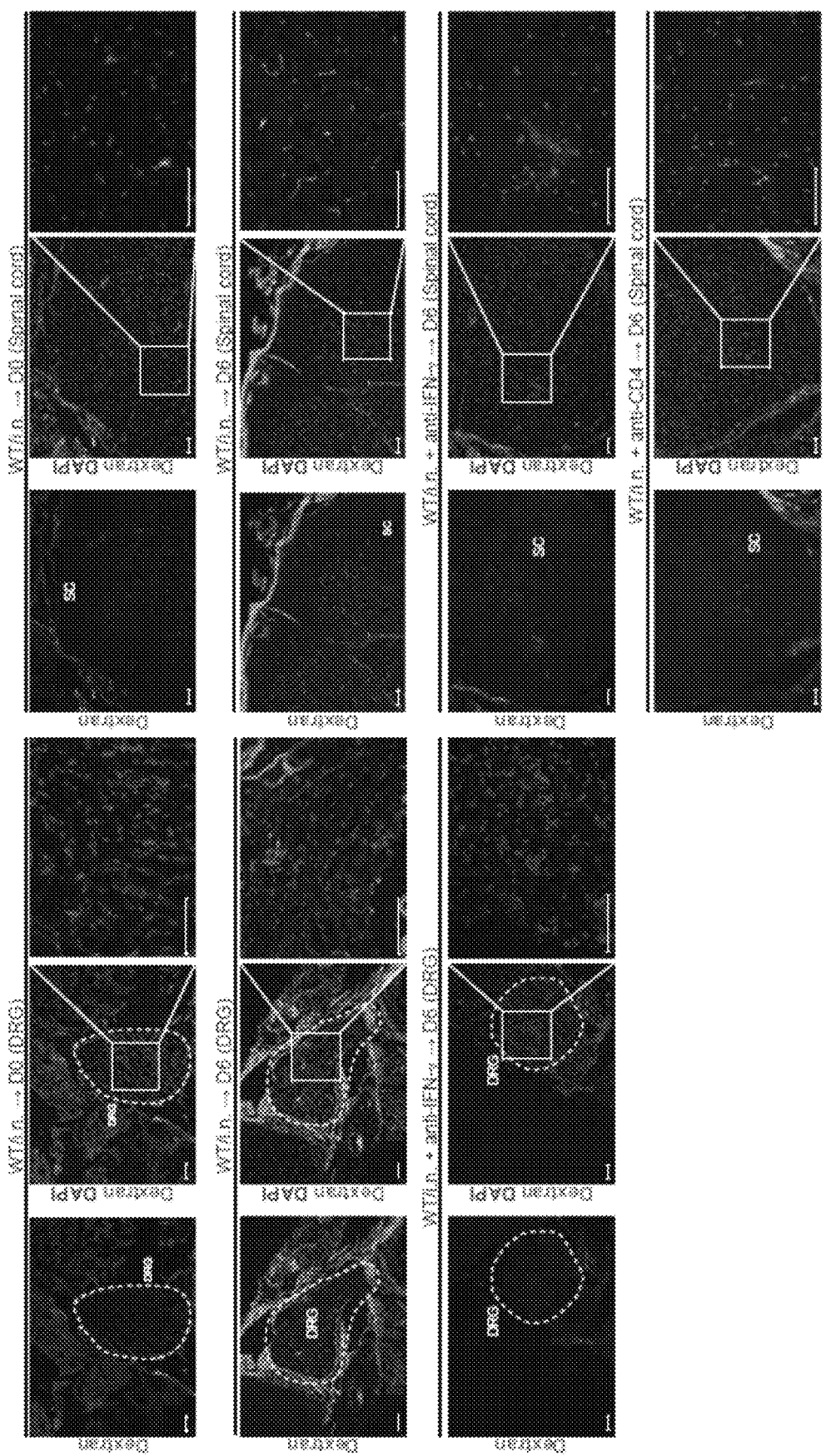

How might IFN-γ secreted by CD4 T cells enable circulating antibody to access the neuronal tissues? IFN-γ acts on the endothelial cells to remodel tight junctions and increase permeability (Capaldo, C. T. et al. 2014, Mol. Biol. Cell 25, 2710-2719). It was observed that recombinant IFN-γ injected intravaginally was sufficient to enable antibody access to the vaginal lumen, suggesting that IFN-γ is sufficient to induce both vascular and epithelial permeability in peripheral tissues (FIG. 12A) and to enhance VCAM-1 expression on endothelial cells (FIG. 12B). To assess whether antibody access to the neuronal tissues mediated by CD4 T cells and IFN-γ is through increased vascular permeability, the measured release of blood albumin into the neuronal tissue following genital HSV-2 challenge in intranasally immunized mice was demonstrated. Notably, it was observed that vascular permeability occurred in the DRG and spinal cord in a CD4 T-cell- and IFN-γ-dependent manner, as measured by leakage of blood albumin to the neuronal tissues by ELISA and immunohistochemical analysis (FIG. 4F and FIG. 13A). It was confirmed that CD4-dependent vascular permeability to the DRG and the spinal cord using intravenous injection of 70 kDa fluorescein isothiocyanate (FITC)-dextran, which has a similar size to IgG (FIG. 13B). Collectively, the results support the notion that CD4 T cells enable antibody delivery to the sites of infection by secreting IFN-γ and enhancing microvascular permeability. This mechanism of antibody delivery is crucial for host immune protection, as depletion of CD4 T cells, inhibition of CD4 T-cell migration into the neuronal tissues or neutralization of IFN-γ renders immune mice susceptible to infection.

Figure 14A:
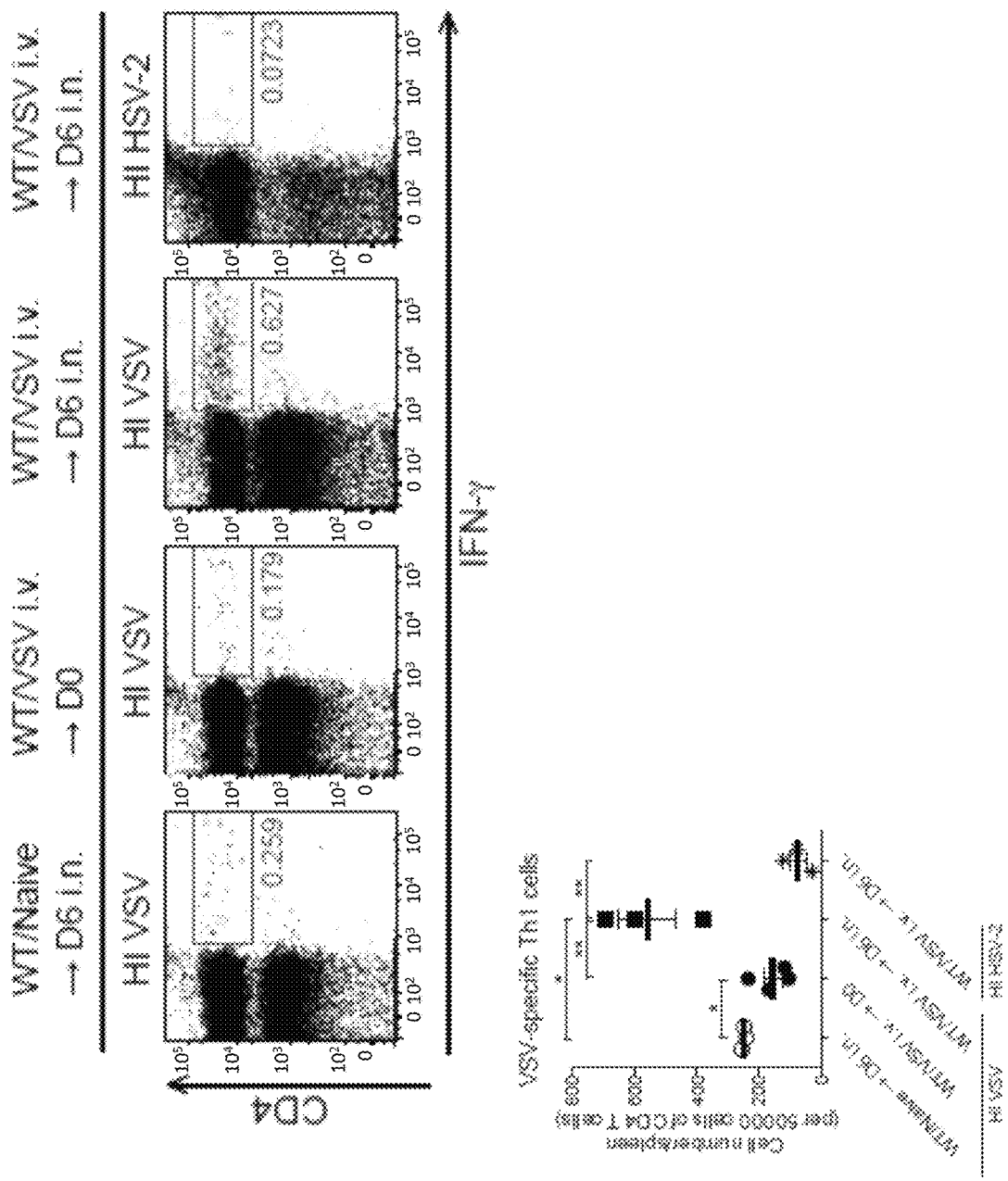
FIG. 14A through FIG. 14D are a set of images depicting the results of experiments demonstrating the requirement of memory CD4+ T cells for the increase in antibody levels and vascular permeability in the brain following VSV immunization and challenge.
Figure 14B:
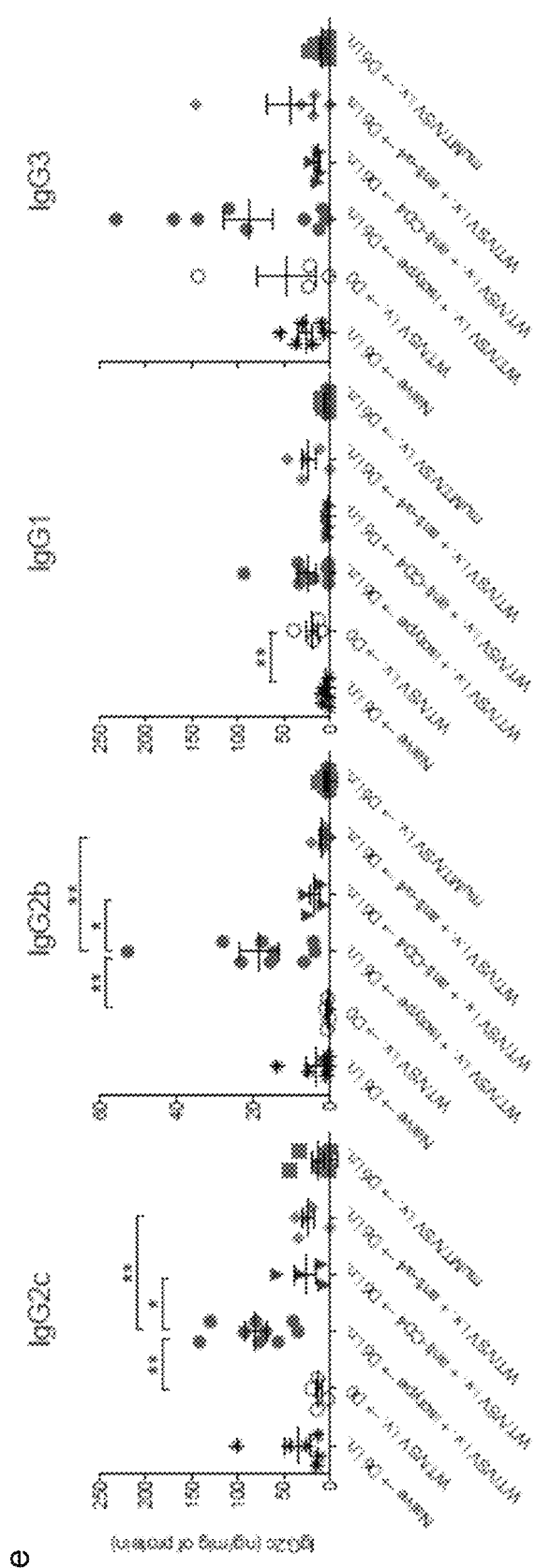
Figure 14C:
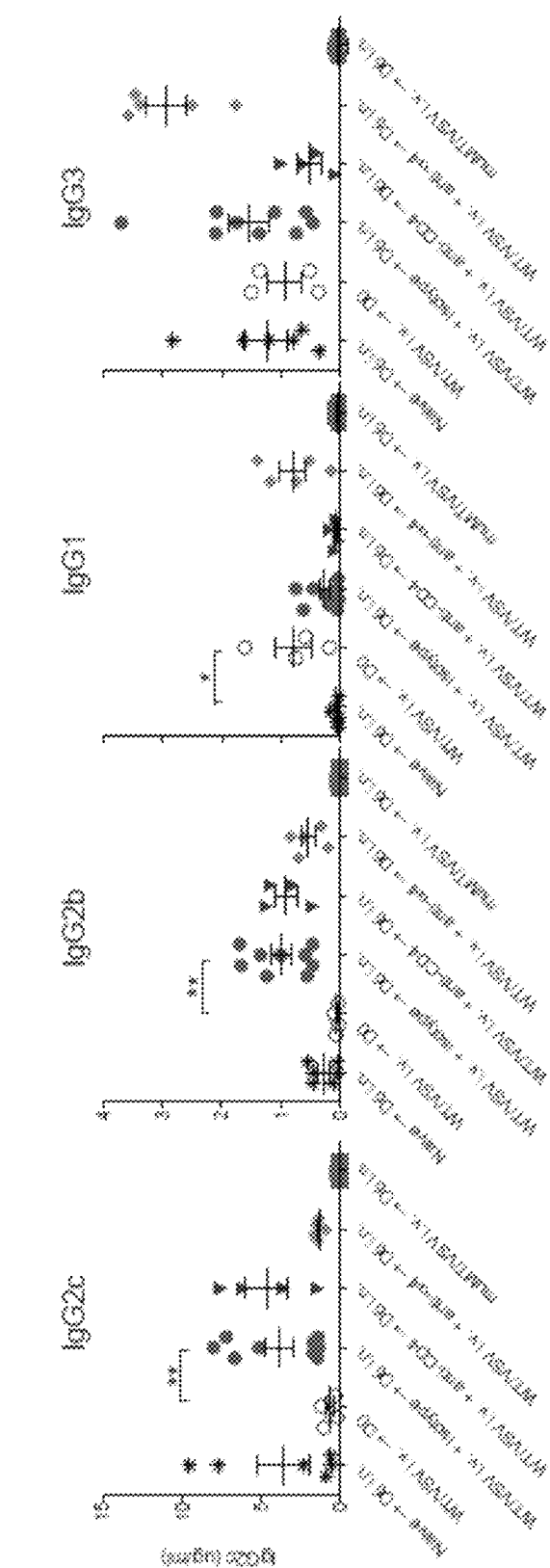
Figure 14D:
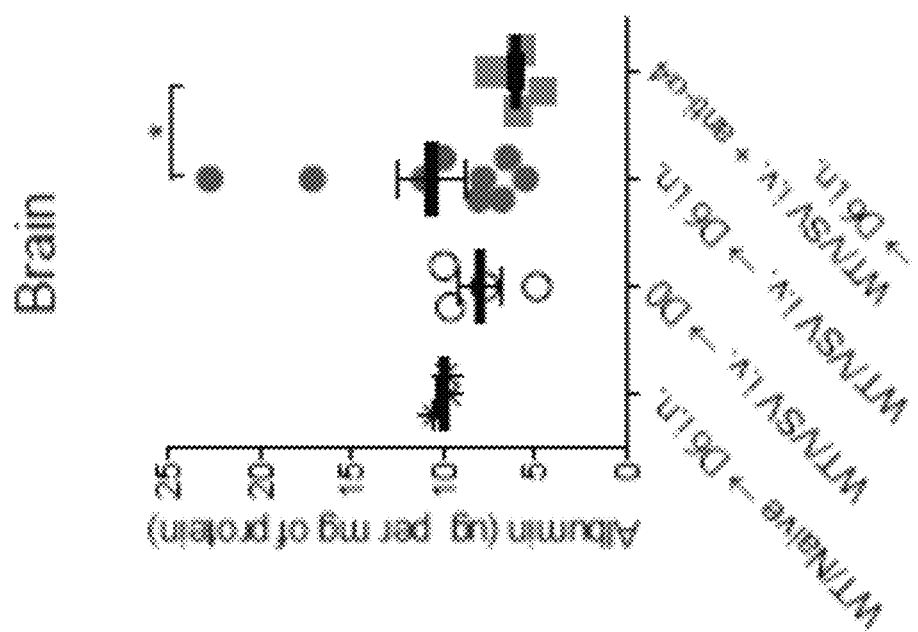

To determine whether the findings extend beyond HSV-2, the determination of antibody access to the neuronal tissue following a different neurotropic virus, vesicular stomatitis virus (VSV), a negative sense RNA virus of the Rhabdoviridae family, was investigated. Upon intranasally inoculation, VSV infects olfactory sensory neurons in the nasal mucosa and enters the CNS through the olfactory bulb (Reiss, C. S. et al., 1998, Ann. NY Acad. Sci. 855, 751-761). In contrast, intravenous infection with VSV is well tolerated, and generates robust T- and B-cell responses (FIG. 14A-FIG. 14D) (Thomsen, A. R. et al., 1997, Int. Immunol. 9, 1757-1766). To determine whether antibody access to the brain requires memory CD4 T cells, mice were immunized with VSV intravenously. Five weeks later, immunized mice were challenged with VSV intranasally. Entry of VSV-specific antibodies was monitored in the brain 6 days after intranasal challenge. Consistent with the data obtained from HSV-2 infection, a striking dependence on CD4 T cells of antibody access to the brain was observed (FIG. 14B). Further, anti-α4 antibody treatment of mice immediately before intranasal VSV challenge also diminished antibody access to the brain, without impacting VSV-specific antibodies in circulation (FIG. 14C). Furthermore, it was determined that vascular permeability to the brain was dependent on α4 integrin, as antibody blockade of α4 integrin resulted in diminished albumin leakage to the brain (FIG. 14D). Taken together, these results indicate that the requirement for α4-integrin and memory CD4 T cells for antibody access applies to two distinct neurotropic viruses, HSV-2 and VSV, and suggest a general mechanism of antibody access to the immunoprivileged tissues protected by the blood-nerve barriers.

These results demonstrate a role of CD4 T cells in controlling antibody access to neuronal tissues through local migration and secretion of IFN-γ. Circulating CD4 memory T cells effectively target antibody delivery to the sites of infection through their secretion of IFN-γ, presumably upon recognition of cognate antigenic peptides presented by local antigen-presenting cells (Laidlaw, B. J. et al., 2014, Immunity 41, 633-645, Iijima, N. et al., 2008, J. Exp. Med. 205, 3041-3052). These results indicate the requirement for CD4 T-cell help at the effector phase of the antibody response, and add to the growing appreciation of CD4 T cells in paving the way to other effector cell types such as CD8 T cells (Laidlaw, B. J. et al., 2014, Immunity 41, 633-645), Nakanishi, Y. et al., 2009, Nature 462, 510-513), Reboldi, A. et al., 2009, Nature Immunol. 10, 514-523). The experimental data demonstrates that the requirement for CD4 T cells for antibody access in neuronal tissue reflects an additional layer of control imposed by the immunoprivileged sites. In accessible tissues, inflammatory leukocytes can migrate and, in response to PAMPs, secrete cytokines such as TNF-α that are sufficient to trigger vascular permeability independently of CD4 T cells. However, after neurotropic viral infections, the infected neurons are expected to be poor at producing inflammatory cytokines that remodel vascular tight junctions. At the same time, recruitment of innate leukocytes is blocked by shutdown of specific chemokines in the ganglia of HSV-1-infected mice (Stock, A. et al., 2014, J Exp. Med. 211, 751-759). Curiously, expression of T-cell-trophic chemokines CXCL9 and CXCL10 was preserved in the DRG of infected mice (Stock, A. et al., 2014, J. Exp. Med. 211, 751-759), suggesting that access by lymphocytes is permitted. Thus, in neuronal tissues, the entry of viral-specific CD4 T cells is crucial to provide cytokines that permit antibodies through the induction of vascular permeability.

The results implicate that antibody-based vaccines or treatment against neurotropic viruses would benefit from generating robust circulating CD4 T-cell memory responses.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for aiding access of an antibody or antibody fragment to immunoprivileged tissue in a subject having a pathological infection of an immuoprivileged tissue comprising:

a.) administering an immunogenic agent intranasally to the subject to induce a immune response in the subject; and b.) administering an antibody or antibody fragment to the subject, whereby the immune response allows access of the antibody or antibody fragment to the immunoprivileged tissue.

2. The method of claim 1, wherein the immunogenic agent is a vaccine for a virus selected from the group consisting of Zika virus, Ebola virus, Japanese encephalitis virus, mumps virus, measles virus, rabies virus, vesicular stomatitis virus (VSV), Epstein-Barr virus (HHV-4), cytomegalovirus, herpes simplex virus 1 (HSV-1), herpes simplex virus 2 (HSV-2), human immunodeficiency virus-1 (HIV-1), JC virus, arborviruses, enteroviruses, West Nile virus, dengue virus, poliovirus, and varicella zoster virus.

3. The method of claim 1, wherein the immunogenic agent comprises an antigenic peptide of a virus selected from the group consisting of Zika virus, Ebola virus, Japanese encephalitis virus, mumps virus, measles virus, rabies virus, vesicular stomatitis virus (VSV), Epstein-Barr virus (HHV-4), cytomegalovirus, herpes simplex virus 1 (HSV-1), herpes simplex virus 2 (HSV-2), human immunodeficiency virus-1 (HIV-1), JC virus, arborviruses, enteroviruses, West Nile virus, dengue virus, poliovirus, and varicella zoster virus.

4. The method of claim 1, wherein the is an antibody or antibody fragment binds to an antigen associated with a virus selected from the group consisting of Zika virus, Ebola virus, Japanese encephalitis virus, mumps virus, measles virus, rabies virus, vesicular stomatitis virus (VSV), Epstein-Barr virus (HHV-4), cytomegalovirus, herpes simplex virus 1 (HSV-1), herpes simplex virus 2 (HSV-2), human immunodeficiency virus-1 (HIV-1), JC virus, arborviruses, enteroviruses, West Nile virus, dengue virus, poliovirus, and varicella zoster virus.

5. The method of claim 4, wherein the antigen associated with the disease or disorder is different from the antigen of the immunogenic agent.

6. The method of claim 1, wherein the immune response comprises the activation or production of memory CD4 T cells.

7. The method of claim 1, wherein the subject has a viral infection.

8. The method of claim 1, wherein the method aids in the access of the antibody or antibody fragment to treat infection-associated inflammation.

9. The method of claim 1, wherein the method aids in the access of the antibody or antibody fragment to treat an infection-associated condition selected from the group consisting of: encephalitis, meningitis, meningoencephalitis, epidural abscess, subdural abscess, brain abscess, and progressive multifocal leukoencephalopathy (PML).

10. The method of claim 1, wherein the immunoprivileged tissue is selected from the group consisting of: brain, spinal cord, peripheral nervous system, testes, eye, placenta, and liver.

11. The method of claim 1, wherein the subject has a bacterial infection.

* * * * *